United States Patent
Moreaux et al.

(10) Patent No.: US 11,578,369 B2
(45) Date of Patent: Feb. 14, 2023

(54) METHOD FOR THE IN VITRO PROGNOSIS OF INDIVIDUALS HAVING MULTIPLE MYELOMA AND METHOD FOR THE TREATMENT THEREOF

(71) Applicants: CENTRE NATIONAL DE LA RECHERCHE SCIENTIFIQUE, Paris (FR); UNIVERSITE DE MONTPELLIER, Montpellier (FR)

(72) Inventors: Jérôme Moreaux, Montpellier (FR); Laurie Herviou, Montpellier (FR); Alboukadel Kassambara, Montpellier (FR); Giacomo Cavalli, Montpellier (FR)

(73) Assignees: CENTRE NATIONAL DE LA RECHERCHE SCIENTIFIQUE, Paris (FR); UNIVERSITE DE MONTPELLIER, Montpellier (FR)

(*) Notice: Subject to any disclaimer, the term of this patent is extended or adjusted under 35 U.S.C. 154(b) by 492 days.

(21) Appl. No.: 16/346,659

(22) PCT Filed: Oct. 31, 2017

(86) PCT No.: PCT/EP2017/077887
§ 371 (c)(1),
(2) Date: May 1, 2019

(87) PCT Pub. No.: WO2018/083086
PCT Pub. Date: May 11, 2018

(65) Prior Publication Data
US 2020/0063209 A1    Feb. 27, 2020

(30) Foreign Application Priority Data
Nov. 2, 2016   (EP) .................... 16306436

(51) Int. Cl.
*C12Q 1/68*      (2018.01)
*C12Q 1/6886*    (2018.01)
*G16H 50/30*     (2018.01)
*G16B 40/10*     (2019.01)

(52) U.S. Cl.
CPC .......... *C12Q 1/6886* (2013.01); *G16B 40/10* (2019.02); *G16H 50/30* (2018.01); *C12Q 2600/106* (2013.01); *C12Q 2600/112* (2013.01); *C12Q 2600/118* (2013.01)

(58) Field of Classification Search
CPC ................................................ C12Q 1/68
See application file for complete search history.

(56) References Cited

FOREIGN PATENT DOCUMENTS

WO    2014/056928 A1    4/2014

OTHER PUBLICATIONS

Hernando et al., "EZH2 inhibition blocks multiple myeloma cell growth through upregulation of epithelial tumor suppressor genes", 2016 Cancer Biol and Signal Trans 15(2):pp. 287. (Year: 2016).*
Knight et al. IMiDs: A Novel Class of Immunomodulators, 2005 Semin Oncol 32(sup 5): S24-S30 (Year: 2005).*
Jones et al., "The safety of pomalidomide for the treatment of multiple myeloma", (2016) Expert Opinion on Drug Safety, 15(4): 535-547 (Year: 2016).*
Xu et al, "Selective inhibition of EZH2 and EZH1 enzymatic activity by a small molecule suppresses MLL-rearranged leukemia" (2015) Myeloid Neoplasia, Blood 125(2): 346-357 (Year: 2015).*
Hernando et al., "EZH2 Inhibition Blocks Multiple Myeloma Cell Growth through Upregulation of Epithelial Tumor Suppressor Genes", 2016 Cancer Biol and Signal Trans 15(2): 287-298. (Year: 2016).*
Kalff et al., "Roar: A Phase Ib Trial of Oral Azacitidine in Combination with Lenalidomide and Dexamethasone for Relapsed Multiple Myeloma (MM) Patients Refractory to Prior Lenalidomide", (2015) Blood 126(23): 3033 (Year: 2015).*
Arora et al., "Abstract PR09: EZH2 inhibitors reveal broad EZH2 dependencies in multiple myeloma", (2016) Cancer Res 76(2Suppl): Abstract, (Year: 2016).*
International Search Report and Written Opinion of the International Searching Authority dated Dec. 11, 2017 in corresponding International application No. PCT/EP2017/077887; 15 pages.
Herviou, et al., "EZH2 in normal hematopoiesis and hematological malignancies", Oncotarget, 2016, p. 2284-2296, vol. 7; 13 pages.
Moreaux, et al.,"A high-risk signature for patients with multiple myeloma established from the molecular classification of human myeloma cell lines", Haematologica, 2010, p. 574-582, vol. 96; 9 pages.
Chen, et al., "Low-risk identification in multiple myeloma using a new 14-gene model", European Journal of Haematology, 2012, p. 28-36, vol. 89; 9 pages.
Knutson, et al., "Synergistic Anti-Tumor Activity of EZH2 Inhibitors and Glucocorticoid Receptor Agonists in Models of Germinal Center Non-Hodgkin Lymphomas", PLOS One, 2014, p. 1-22; 22 pages.
Momparler, et al., "Targeting of cancer stem cells by inhibitors of DNA and histone methylation", Expert Opinion on Investigational Drugs, 2015, p. 1031-1043, vol. 24, No. 8; 14 pages.

(Continued)

*Primary Examiner* — Jehanne S Sitton
(74) *Attorney, Agent, or Firm* — Maier & Maier, PLLC

(57) ABSTRACT

A method for in vitro predicting of the outcome of an individual having a multiple myeloma, including the steps of: a) measuring the expression level of at least 5 genes and/or proteins encoded by the 5 genes, the genes being selected in a group including NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from the individual; b) calculating a score value from the expression level obtained at step a); c) classifying the individual as having a good prognosis status or a bad prognosis status, by comparing the score value obtained at step b) with a reference score value.

6 Claims, 8 Drawing Sheets

(56) References Cited

OTHER PUBLICATIONS

Dimopoulos, et al., "Dual Inhibition of DNMT1 and EZH2 Can Effectively Overcome Both Intrinsic and Acquired Resistance of Myeloma Cells to IMIDS", 2017; URL: https//learningcenter.ehaweb.org/eha/ 2017/22nd/181611/konstantinos.dimopoulos.dual.inhibition.of.dnmtl.and.ezh2.can.efrec tively.html; retrieved on Nov. 28, 2017; 3 pages.

Peng, et al., "Epigenetic silencing of TH1-type chemokines shapes tumour immunity and immunotherapy", Nature, 2015, p. 249-253, vol. 527, No. 7577; 16 pages.

Knutson, et al., "Selective Inhibition of EZH2 by EPZ-6438 Leads to Potent Antitumor Activity in EZH2-Mutant Non-Hodgkin Lymphoma", Molecular Cancer Therapeutics, 2014, p. 842-854, vol. 13, No. 4; 14 pages.

Kim, et al., "Targeting EZH2 in cancer", nature medicine, 2016, p. 128-134, vol. 22, No. 2; 7 pages.

Barallon, et al., "Recommendation of short tandem repeat profiling for authenticating human cell lines, stem cells, and tissues", In Vitro Cellular & Developmental Biology—Animal, 2010, p. 727-732, vol. 46; 6 pages.

Dobin, et al., "STAR: ultrafast universal RNA-seq aligner", Bioinformatics, 2013, p. 15-21, vol. 29, No. 1; 7 pages.

Hose, et al., "Proliferation is a central independent prognostic factor and target for personalized and risk-adapted treatment in multiple myeloma", haematologica, 2011, p. 87-95, vol. 96; 9 pages.

Hose, et al., "Inhibition of aurora kinases for tailored risk-adapted treatment of multiple myeloma", Blood, 2009, p. 4331-4340, vol. 113; 11 pages.

Knight, "IMiDs: A Novel Class of Immunomodulators", Seminars in Oncology, 2005, p. S24-S30; 7 pages.

Love, et al., "Moderated estimation of fold change and dispersion for RNA-seq data with DESeq2", Genome Biology, 2014, p. 1-21, vol. 15; 21 pages.

Moreaux, et al., "TACI expression is associated with a mature bone marrow plasma cell signature and C-MAF overexpression in human myeloma cell lines", Haematologica, 2007, p. 803-811, vol. 92; 9 pages.

Moreaux, et al., "Development of Gene Expression-Based Score to Predict Sensitivity of Multiple Myeloma Cells to DNA Methylation Inhibitors", Molecular Cancer Therapeutics, 2012, p. 2685-2692, vol. 11; 9 pages, Jul. 1, 2021.

Mulligan, et al., "Gene expression profiling and correlation with outcome in clinical trials of the proteasome inhibitor bortezomib", blood, 2007, p. 3177-3188, vol. 109; 13 pages.

Yu, et al., "ReactomePA: an R/Bioconductor package for reactome pathway analysis and visualization", Molecular BioSystems, 2016, p. 477-479; 8 pages.

* cited by examiner

METHOD FOR THE IN VITRO PROGNOSIS OF INDIVIDUALS HAVING MULTIPLE MYELOMA AND METHOD FOR THE TREATMENT THEREOF

FIELD OF THE INVENTION

The present invention relates to the prognosis of individuals having multiple myeloma (MM) and the prediction of the likelihood of said individuals to positively respond to a targeted therapeutic treatment.

More particularly, the invention relies upon the determination of a score for each MM individual, intended to assist a physician to evaluate the stage of the MM disease, to predict the outcome of MM individuals and to assess the likelihood of said individuals to positively respond to a therapeutic treatment comprising an inhibitor of enhancer of zest homologue 2 (EZH2).

BACKGROUND OF THE INVENTION

Multiple myeloma (MM) is the second most common blood cancer, and is affecting the plasma cells. In individuals having multiple myeloma, malignant clonal plasma cells accumulate within the bone marrow. These aberrant cells are 'diluting' the normal plasma cells that are devoted to fight infections. The malignant plasma cells also produce abnormal proteins, such as M protein, which may cause solid tumors, damage the kidneys, and impair immune system function. In some cases, the malignant cells may cause a single tumor, called a solitary plasmacytoma, but if multiple tumors are formed, and then the disease is called multiple myeloma.

MM affects approximately 25,000 new individuals per year in the EU, accounts for 10% of hematological malignancies and 1.6% of all cancer deaths in the US.

MM is a very heterogeneous disease, at the molecular as well as the clinical level. At diagnosis, patients are classified into different subgroups depending on the MMCs molecular discrepancies and on different transcriptome/biomarkers-based scores, each associated to a given outcome.

Genome sequencing studies have recently revealed considerable heterogeneity and genomic instability, a complex mutational landscape and a branching pattern of clonal evolution. Epigenetic markers, such as DNA methylation or histone posttranslational modifications, could also be involved in MM pathophysiology and drug resistance.

Although it was considered incurable for a long time, recent developments in cancer research have provided treatment strategies leading to an overall survival of intensively-treated patients of 6-7 years and an event-free survival of 3-4 years. However, patients invariably relapse after multiple lines of treatment, with shortened intervals in between relapses, and finally become resistant to any treatment, resulting in loss of clinical control over the disease and death within weeks.

Despite these recent advances in cancer research, the proposed therapeutic approaches often depend on the patient's age only, and thus are not adapted to an individual patient or even a subgroup of patients.

Taken into account the current growing tendency for therapy providers in developing personalized diagnostic and therapeutic approaches, there is therefore an urgent need to provide individuals having MM with an accurate diagnosis of the disease intended to lead to the most adapted treatment.

SUMMARY OF THE INVENTION

One aspect of the invention relates to a method for in vitro predicting the outcome of an individual having a multiple myeloma, comprising the steps of:
  a) measuring the expression level of at least 5 genes and/or proteins encoded by the said 5 genes, the said at least 5 genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from said individual;
  b) calculating a score value from said expression level obtained at step a);
  c) classifying the said individual as having a good prognosis status or a bad prognosis status, by comparing the score value obtained at step b) with a reference score value.

Another aspect of the invention relates to a method for in vitro predicting the likelihood of an individual having a multiple myeloma to respond to a therapeutic treatment comprising an inhibitor of enhancer of zest homologue 2 (EZH2), comprising the steps of:
  a) measuring the expression level of at least 5 genes and/or proteins encoded by the said at least 5 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from an individual having a multiple myeloma;
  b) calculating a score value from said expression level obtained at step a);
  c) classifying the said individual as being a responsive individual or a non-responsive individual, by comparing the score value obtained at step b) with a reference score value.

In a still other aspect, the invention relates to a method for in vitro determining the stage of a multiple myeloma disease in an individual having multiple myeloma, comprising the steps of:
  a) measuring the expression level of at least 5 genes and/or proteins encoded by the said at least 5 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from said individual;
  b) calculating a score value from said expression levels obtained at step a);
  c) classifying the said individual as being an early stage individual, an intermediate stage individual or a late stage individual, by comparing the score value obtained at step b) with a reference score value.

Another aspect of the invention concerns a pharmaceutical composition comprising, in a pharmaceutical acceptable vehicle, a combination of an EZH2 inhibitor and one or more active ingredient against multiple myeloma.

In some embodiments of the said pharmaceutical composition, the said one or more active ingredient is selected in the group consisting of immunomodulatory agents and DNA methyltransferase inhibitors.

In some embodiments of the said pharmaceutical composition, the immunomodulatory agent is selected in a group comprising thalidomide, lenalidomide, pomalidomide and a derivative thereof.

In some other embodiments of the said pharmaceutical composition, the DNA methyltransferase inhibitor is selected in a group consisting of 5-azacytidine, zebularine, caffeic acid, CC-486 (azacytidine), chlorogenic acid, epigallocatechin gallate, hydralazine hydrochloride, procaine hydrochloride and RG108.

Another aspect of the invention relates to a pharmaceutical composition comprising, in a pharmaceutical acceptable vehicle, an EZH2 inhibitor, and optionally an immunomodulatory agent.

In still further aspects of the said pharmaceutical composition, the EZH2 inhibitor is selected in a group comprising CPI-169, El-1, EPZ-005687, EPZ-6438 (Tazemetostat), GSK-126, GSK-343, GSK-503, DZNep and UNC-1999.

In yet further embodiments of the said pharmaceutical composition, the EZH2 inhibitor is EPZ-6438 (Tazemetostat) and the immunomodulatory agent is lenalidomide.

In still other embodiments, the said invention pertains to a pharmaceutical composition comprising a combination of an EZH2 inhibitor, an immunomodulatory agent and a DNA methyltransferase inhibitor. In some embodiments, the EZH2 inhibitor is EPZ-6438 (Tazemetostat), the immunomodulatory agent is lenalidomide and the DNA methyltransferase inhibitor is decitabine.

Finally, the invention also relates to a pharmaceutical composition comprising, in a pharmaceutical acceptable vehicle, an EZH2 inhibitor and optionally an immunomodulatory agent, for use in treating a multiple myeloma individual in need thereof.

DETAILED DESCRIPTION OF THE INVENTION

Figure 1:
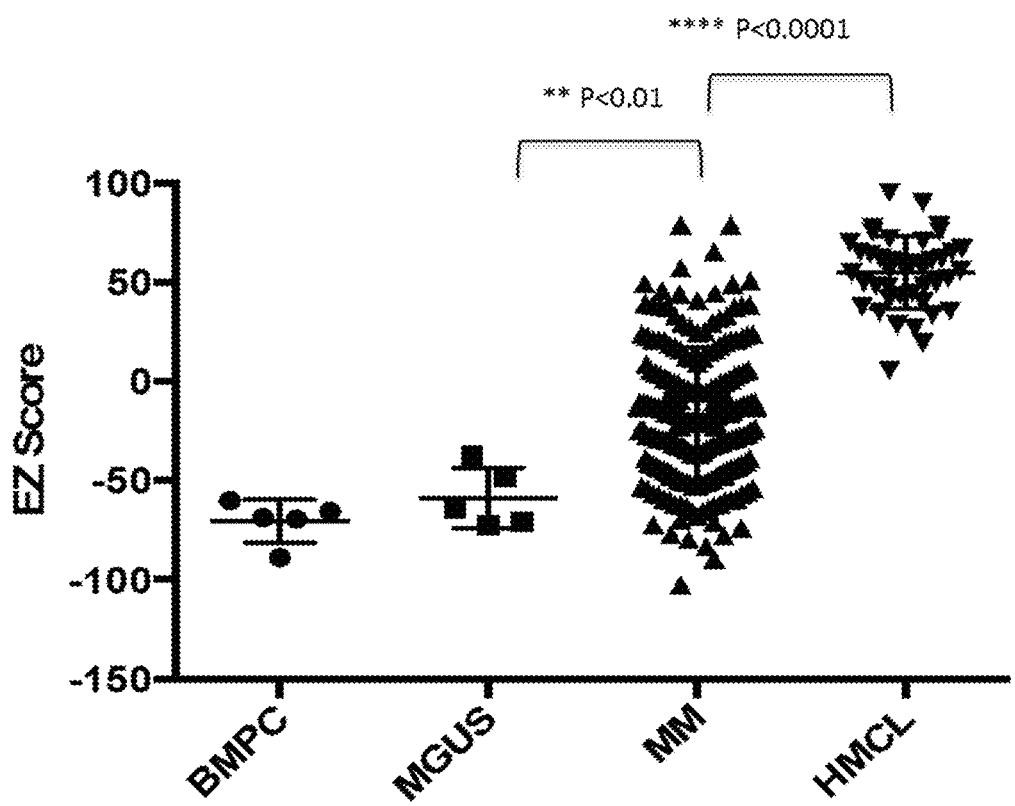
FIG. 1: Diagram illustrating the EZ score in normal bone marrow plasma cells (BMPCs, N=7), in premalignant plasma cells ("PCs") of patients with monoclonal gammopathy of undetermined significance (MGUS, N=5), in multiple myeloma cells of patients with intramedullary multiple myeloma (MM, N=206) and in human myeloma cell lines (HMCLs, N=40). Results were compared with a Student t-test.

The inventors have identified a set of a plurality of genes and/or proteins, which are differentially expressed in individuals having a multiple myeloma as compared to healthy individuals. A score value may be calculated, taking into account the beta coefficient for each gene or protein, based on the Cox statistical model. Said score may be advantageously implemented for prognosis purposes, i.e. to assist physicians classifying individuals between poor prognosis status individuals and good prognosis status individuals.

In particular, the inventors could show that the score value obtained from individuals having a multiple myeloma significantly correlates with the ability of said individuals to respond to a targeted therapeutic treatment. Indeed, individuals with poor prognosis status were prone to respond to an inhibitor of EZH2 histone methyltransferase.

In addition, the inventors show that the treatment with an IMiD ("Immunomodulator drug", which is a compound that is derived from thalidomide) of MM individuals may be potentialized by a pre-treatment with an inhibitor of a histone methyltransferase, in particular EZH2 histone methyltransferase.

Still further, the inventors have shown that a treatment of MM individuals, having a multiple myeloma that is resistant to an EZH2 inhibitor, with a DNA methyltransferase inhibitor allows re-sensitizing the EZH2 inhibitor-resistant MM cells to the action to EZH2 inhibitors. More precisely, it is shown in the examples herein that a sublethal dose of a DNA methyltransferase inhibitor re-sensitizes EZH2 inhibitor-resistant MM cells to the action of EZH2 inhibitors. It is specified that the terms "DNA methyltransferase inhibitor" and "DNA hypomethylation agent" may be interchangeably used herein.

Without wishing to be bound by any particular theory, the inventors believe that the prognosis score, which is based on the expression profile of the set of genes and/or proteins disclosed herein, including a set of 5 genes and/or proteins disclosed herein, which encompasses a set of 15 genes disclosed herein, reflect the degree of severity of the multiple myeloma disease, and therefore provide a tool for implementing the personalized medicine concept.

Within the scope of the present invention, the term "individual" refers to a mammal individual, preferably a human individual.

The expression "multiple myeloma individual" refers to an individual having a multiple myeloma.

The expression "multiple myeloma" refers to the multiple myeloma disease such as defined by class C90.0 in accordance with the International Classification of Diseases World Health Organisation Classification (10th revised edition; 2016).

The term "outcome" refers to the survival, the relapse or the death of the individual. The outcome may relate to disease-free survival (DFS), event free survival (EFS) or overall survival (OS), as defined within the state of the art. Illustratively, a "bad outcome" may refer to a disease relapse or death of the individual. Oppositely, a "good outcome" may refer to survival of the individual, with or without relapse episode.

The NRP2 gene (Entrez Gene 8828) encodes the NRP2 protein (UniProtKB O60462), a member of the neuropilin family of receptor proteins. NRP2 is also known as Neuropilin 2, Vascular Endothelial Cell Growth Factor 165 Receptor 2, VEGF165R2, Receptor For VEGF165 And Semaphorins Class3, Neuropilin-2a(17), Neuropilin-2a(22), Neuropilin-2b(0), PRO2714, NPN2 or NP2.

The REEP1 gene (Entrez Gene 65055) encodes the REEP1 protein (UniProtKB Q9H902), a mitochondrial protein that functions to enhance the cell surface expression of odorant receptors. REEP1 is also known as Receptor Accessory Protein 1, C2orf2, Receptor Expression Enhancing Protein 1, Chromosome 2 Open Reading Frame 23, HMN5B, SPG31 or Yip2a.

The SV2B gene (Entrez Gene 9899) encodes the SV2B protein (UniProtKB Q7LII2). SV2B is also known as Synaptic Vesicle Glycoprotein 2B, Synaptic Vesicle Protein 2B Homolog, HsT19680 or KIAA0735.

The ARRB1 gene (Entrez Gene 408) encodes the ARRB1 protein (UniProtKB P49407), a member of arrestin/beta-arrestin protein family. ARRB1 is also known as Arrestin Beta 1, Arrestin 2, ARR1 or ARB1.

The CACNA1G gene (Entrez Gene 8913) encodes the CACNA1G protein (UniProtKB O43497), a T-type, low-voltage activated calcium channel. CACNA1G is also known as Calcium Voltage-Gated Channel Subunit Alpha1 G; Calcium Channel, Voltage-Dependent, T Type, Alpha 1G Subunit; Voltage-Gated Calcium Channel Subunit Alpha Cav3.1; Cav3.1c; NBR13; Ca(V)T.1; KIAA1123; Cav3.1 or SCA42.

The FBLIM1 gene (Entrez Gene 54751) encodes the FBLIM1 protein (UniProtKB Q8WUP2), a protein with an N-terminal filamin-binding domain, a central proline-rich domain, and, multiple C-terminal LIM domains. FBLIM1 is also known as Filamin Binding LIM Protein 1, Mitogen-Inducible 2-Interacting Protein, MIG2-Interacting Protein, Migfilin, FBLP-1, FBLP1, Mitogen-Inducible 2 Interacting Protein, Filamin-Binding LIM Protein-1, CSX-Associated LIM and CAL.

The FGFR1 gene (Entrez Gene 2260) encodes the FGFR1 protein (UniProtKB P11362), a member of the fibroblast growth factor receptor (FGFR) family. FGFR1 is also known as Fibroblast Growth Factor Receptor 1, Basic Fibroblast Growth Factor Receptor 1, Fms-Related Tyrosine Kinase 2, Proto-Oncogene C-Fgr, EC 2.7.10.1, BFGF-R-1, FGFR-1, N-SAM, BFGFR, FGFBR, FLT-2, HBGFR, FLT2, CEK, FLG, Heparin-Binding Growth Factor Receptor, Hydroxyaryl-Protein Kinase, FMS-Like Tyrosine Kinase 2, Fms-Like Tyrosine Kinase 2, FGFR1/PLAG1 Fusion, Pfeiffer Syndrome, CD331 Antigen, EC 2.7.10, HRTFDS, CD331, ECCL, KAL2, HH2 and OGD.

The IRF6 gene (Entrez Gene 3664) encodes the IRF6 protein (UniProtKB O14896), a member of the interferon regulatory transcription factor (IRF) family. IRF6 is also known as Interferon Regulatory Factor 6, Van Der Woude Syndrome, IRF-6, VWS1, OFC6, PPS1, PPS, PIT, LPS and VWS.

The ITGA9 gene (Entrez Gene 3680) encodes the ITGA9 protein (UniProtKB Q13797), an alpha integrin. ITGA9 is also known as Integrin Subunit Alpha 9, Integrin Alpha-RLC, Integrin Alpha 9, Alpha 4-Like, ALPHA-RLC, Integrin, ITGA4L and RLC.

The NOVA2 gene (Entrez Gene 4858) encodes the NOVA2 protein (UniProtKB Q9UNW9). NOVA2 is also known as Neuro-Oncological Ventral Antigen 2, Astrocytic NOVA1-Like RNA-Binding Protein, Neuro-Oncological Ventral Antigen 3, NOVA3 and ANOVA.

The PPP2R2C gene (Entrez Gene 5522) encodes the PPP2R2C protein (UniProtKB Q9Y2T4), a member of the phosphatase 2 regulatory subunit B family. PPP2R2C is also known as Protein Phosphatase 2 Regulatory Subunit B, Gamma 2; Protein Phosphatase 2 (Formerly 2A), Regulatory Subunit B (PR 52), Gamma Isoform; PP2A Subunit B Isoform Gamma; IMYPNO1; Serine/Threonine-Protein Phosphatase 2A 55 KDa Regulatory Subunit B Gamma Isoform; Protein Phosphatase 2 (Formerly 2A), Regulatory Subunit B, Gamma Isoform; Gamma Isoform Of Regulatory Subunit B55, Protein Phosphatase 2; Phosphoprotein Phosphatase 2A BR Gamma Regulatory Chain; Protein Phosphatase 2, Regulatory Subunit B, Gamma; Protein Phosphatase 2A1 B Gamma Subunit; PP2A, Subunit B, PR55-Gamma Isoform; PP2A, Subunit B, B55-Gamma Isoform; PP2A, Subunit B, R2-Gamma Isoform; PP2A Subunit B Isoform PR55-Gamma; PP2A, Subunit B, B-Gamma Isoform; PP2A Subunit B Isoform B55-Gamma; PP2A Subunit B Isoform R2-Gamma; B55-GAMMA; IMYPNO; PR55G and PR52.

The SLC5A1 gene (Entrez Gene 6523) encodes the SLC5A1 protein (UniProtKB P13866), a member of the sodium-dependent glucose transporter (SGLT) family. SLC5A1 is also known as Solute Carrier Family 5 Member 1; Solute Carrier Family 5 (Sodium/Glucose Cotransporter), Member 1; High Affinity Sodium-Glucose Cotransporter; SGLT1; NAGT; Sodium/Glucose Cotransporter 1; Na(+)/Glucose Cotransporter 1; Na+/Glucose Cotransporter 1 and D22S675.

The SORL1 gene (Entrez Gene 6653) encodes the SORL1 protein (UniProtKB Q92673), a member of the vacuolar protein sorting 10 (VPS 10) domain-containing receptor family, and the low density lipoprotein receptor (LDLR) family. SORL1 is also known as Sortilin-Related Receptor, L(DLR Class) A Repeats Containing; LDLR Relative With 11 Ligand-Binding Repeats; Low-Density Lipoprotein Receptor Relative With 11 Ligand-Binding Repeats; Sorting Protein-Related Receptor Containing LDLR Class A Repeats; C11orf32; SorLA-1; SORLA; LR11; Sortilin-Related Receptor, L(DLR Class) A Repeats-Containing; Chromosome 11 Open Reading Frame 32; Mosaic Protein LR11; Gp250 and LRP9.

The SYT7 gene (Entrez Gene 9066) encodes the SYT7 protein (UniProtKB 043581), a member of the synaptotagmin gene family. SYT7 is also known as Synaptotagmin 7, Synaptotagmin VII, Prostate Cancer-Associated Protein 7, PCANAP7, SYTVII, IPCA-7, Prostate Cancer Associated Protein 7, SYT-VII and IPCA7.

The THY1 gene (Entrez Gene 7070) encodes the THY1 protein (UniProtKB P04216), a cell surface glycoprotein and member of the immunoglobulin superfamily of proteins. THY1 is also known as Thy-1 Cell Surface Antigen, Thy-1 Antigen, CDw90, Thy-1 T-Cell Antigen, CD90 Antigen and CD90.

1/Survival Prognosis

One aspect of the invention relates to a method for in vitro predicting the outcome of an individual having a multiple myeloma, comprising the steps of:
  a) measuring the expression level of at least 5 genes and/or proteins encoded by the said at least 5 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from said individual;
  b) calculating a score value from said expression level obtained at step a);
  c) classifying the said individual as having a good prognosis status or a bad prognosis status, by comparing the score value obtained at step b) with a reference score value.

Within the scope of the present invention, it has to be understood that the expression level of any combination of 2, 3, 4, 5, 6, 7, 8, 9, 10, 11, 12, 13, 14 and 15 genes and/or proteins encoded by the said 2, 3, 4, 5, 6, 7, 8, 9, 10, 11, 12, 13, 14 and 15 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is of special interest.

In other words, each of the combination of 2, 3, 4, 5, 6, 7, 8, 9, 10, 11, 12, 13, 14 and 15 genes and/or proteins encoded by the said 2, 3, 4, 5, 6, 7, 8, 9, 10, 11, 12, 13, 14 and 15 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is explicitly disclosed herein.

In certain embodiments, the expression level of at least 2 genes and/or proteins encoded by the said at least 2 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

In certain embodiments, the expression level of 2, 3, 4, 5, 6, 7, 8 or 9 genes and/or proteins encoded by the said 2, 3, 4, 5, 6, 7, 8 or 9 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

Illustratively, the combination of 2 genes and/or proteins encoded by the said 2 genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is chosen in a group comprising each of the 105 possible combinations.

In some embodiments, the combination of 3 genes and/or proteins encoded by the said 3 genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is chosen in a group comprising each of the 455 possible combinations.

In some embodiments, the combination of 4 genes and/or proteins encoded by the said 4 genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is chosen in a group comprising each of the 1365 possible combinations.

In some embodiments, the combination of 5 genes and/or proteins encoded by the said 5 genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is chosen in a group comprising each of the 3003 possible combinations. The said combination of 5 genes encompasses the combination of the genes ARRB1, CACNA1G, FGFR1, NOVA2 and SV2B.

In some embodiments, the combination of 6 genes and/or proteins encoded by the said 6 genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is chosen in a group comprising each of the 5005 possible combinations.

In some embodiments, the combination of 7 genes and/or proteins encoded by the said 7 genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is chosen in a group comprising each of the 6435 possible combinations.

In some embodiments, the combination of 8 genes and/or proteins encoded by the said 8 genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is chosen in a group comprising each of the 6435 possible combinations.

In some embodiments, the combination of 9 genes and/or proteins encoded by the said 9 genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is chosen in a group comprising each of the 5005 possible combinations.

In certain embodiments, the expression level of at least 10 genes and/or proteins encoded by the said 10 genes encoded by a gene selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

In certain embodiments, the expression level of 11, 12, 13, 14 or 15 genes and/or proteins encoded by the said 11, 12, 13, 14 or 15 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

In some embodiments, the combination of 10 genes and/or proteins encoded by the said 11, 12, 13, 14 or 15 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is chosen in a group comprising each of the 3003 possible combinations.

In some embodiments, the combination of 11 genes and/or proteins encoded by the said 11 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is selected in a group comprising each of the 1365 possible combinations.

In some embodiments, the combination of 12 genes and/or proteins encoded by the said 12 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is selected in a group comprising each of the 465 possible combinations.

In some embodiments, the combination of 13 genes and/or proteins encoded by the said 13 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is selected in a group comprising each of the 105 possible combinations.

In some embodiments, the combination of 14 genes and/or proteins encoded by the said 14 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is selected in a group comprising each of the 15 possible combinations.

In certain preferred embodiments, the expression level of each of the 15 genes and/or proteins consisting of NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

The individual having MM may originate from the general population of MM individuals, from early stage MM individuals, from intermediary stage MM individuals, from late stage MM individuals, from MM individuals not undergoing therapeutic treatment, from MM individuals not undergoing therapeutic treatment but having experienced at least one previous therapeutic treatment, from MM individuals undergoing therapeutic treatment, from MM individuals experiencing a refractory/relapsing MM, and a combination thereof.

Within the scope of the present invention, a "biological sample" refers to a biological sample obtained, reached, collected or isolated from an individual, in vivo or in situ. Such samples may be, but not limited to, organs, tissues, fractions and cells isolated from an individual. For example, suitable biological samples include but are not limited to a cell culture, a cell line, a tissue biopsy such as a bone marrow aspirate, a biological fluid such as a blood, pleural effusion or a serum sample, and the like.

In certain embodiments, the preferred biological sample includes but is not limited to a blood sample, a tissue biopsy, including a bone marrow aspirate.

In some embodiments, the biological sample may be a crude sample.

In some other embodiments, the biological sample may be purified to various degrees prior to storage, processing, or measurement.

The expression level of the defined set of genes and/or proteins may be measured by the mean of any technique used in the field.

In some embodiments, the expression level of a gene of interest may be measured through the quantification of the level of mRNA expression.

In some embodiments, the level of mRNA expression for each of the genes of interest may be performed using the well-known techniques available in the state of the art.

Illustratively, mRNA may be extracted, for example using lytic enzymes or chemical solutions or extracted by commercially available nucleic-acid-binding resins following the manufacturer's instructions. Extracted mRNA may be subsequently detected by hybridization, such as Northern blot, and/or amplification, such as quantitative or semi-quantitative RT-PCR. Other methods of amplification include ligase chain reaction (LCR), transcription-mediated amplification (TMA), strand displacement amplification (SDA) and nucleic acid sequence based amplification (NASBA).

In some embodiments, the level of mRNA expression for each of the genes of interest may be measured by the mean of quantification of the cDNA synthesized from said mRNA, as a template, by one reverse transcriptase.

Methods for determining the quantity of mRNA by microarrays or by RNA sequencing may also be used.

In certain embodiments, complexes between the double-stranded nucleic acids resulting from amplification and fluorescent SYBR® molecules may be obtained and then the fluorescence signal generated by the SYBR® molecules complexed with the said amplified nucleic acids may be measured.

Identification of suitable primers that are specific for each of the genes mRNA consists of a routine work for the one skilled in the art.

In certain embodiments, detection by hybridization may be performed with a detectable label, such as fluorescent probes, radioactive probes, enzymatic reactions or other ligands (e.g. avidin/biotin).

Protein expression level may be measured by well-known techniques including detection and quantification of the protein of interest by the means of any type of ligand molecule that specifically binds thereto, including nucleic acids (for example nucleic acids selected for binding through the well-known SELEX method), antibodies and antibody fragments.

Yet illustratively, antibodies to said given protein of interest may be easily obtained with the conventional techniques, including generation of antibody-producing hybridomas.

Hybridomas prepared by conventional techniques are then screened using standard methods to identify one or more hybridomas which produce an antibody which specifically binds with the biological marker protein or a fragment thereof. The invention also encompasses hybridomas made by this method and antibodies made using such hybridomas.

Polyclonal antibodies may be used as well.

Thus, in preferred embodiments, expression of a marker is assessed using for example:
- a radio-labelled antibody, in particular, a radioactive moiety suitable for the invention may for example be selected within the group comprising $^3H$, $^{121}I$, 1231, $^{99m}Tc$, $^{14}C$ or $^{32}P$;
- a chromophore-labelled or a fluorophore-labelled antibody, wherein a luminescent marker, and in particular a fluorescent marker, suitable for the invention may be any marker commonly used in the field such as fluorescein, BODIPY, fluorescent probes type ALEXA, coumarin and its derivatives, phycoerythrin and its derivatives, or fluorescent proteins such as GFP or the DsRed;
- a polymer-backbone-antibody;
- an enzyme-labelled antibody, said labelling enzyme suitable for the invention may be an alkaline phosphatase, a tyrosinase, a peroxydase, or a glucosidase; for example, suitable avidin-labelled enzyme may be an avidin-Horse Radish Peroxydase (HRP), and a suitable substrate may be AEC, 5-bromo-4-chloro-3-indolyl phosphate (BCIP), nitro blue tetrazolium chloride (NBT);
- an antibody derivative, for example an antibody conjugated with a substrate or with the protein or ligand of a protein-ligand pair, in particular a biotin, a streptavidin or an antibody binding the polyhistidine tag;
- an antibody fragment, for example a single-chain antibody, an isolated antibody hypervariable domain, etc., which binds specifically to a marker protein or a fragment thereof, including a marker protein which has undergone all or a portion of its normal post-translational modification.

In vitro techniques for detection of a biological marker protein include enzyme linked immunosorbent assays (ELISAs), Western blots, immunoprecipitations and immunofluorescence.

The expression level for each combination of genes and/or protein of interest may be associated with a score value.

Illustratively, following the measurement of the expression level of at least 2 or more genes and/or proteins encoded by the said 2 or more genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from an individual having MM (step a) of the method), the computation of a score value may be performed be a method comprising the following steps:
i) comparing the expression level determined at step a) with a predetermined reference expression level (PREL);
ii) calculating the score value with the following formula:

$$Score = \sum_{i=1}^{n} \beta i \times Ci$$

wherein:
n represents the number of genes and/or protein which expression level is measured, i.e. n being comprised from 2 to 15,
βi represents the regression β coefficient reference value for a given gene or protein, and
Ci represents 1 if the expression level of said gene or protein is higher than the predetermined reference level (PREL) or Ci represents −1 if the expression level of the gene or the protein is lower than or equal to the predetermined reference level (PREP).

The predetermined reference level (PREL) is often referred as to "maxstat value" or "maxstat cutpoint".

In some embodiments, a good prognosis status refers to an individual having a score value lower than or equal to a predetermined reference value (PRV).

In some embodiments, a bad prognosis status refers to an individual having a score value higher than a predetermined reference value (PRV).

In certain embodiments, the individual having a bad prognosis status is likely to display a bad outcome.

The regression β coefficient reference value may be easily determined by the skilled man in the art for each gene or protein using the well-known statistical Cox model, which is based on a modelling approach to analyse survival data. The purpose of the model is to simultaneously explore the effects of several variables on survival. When it is used to analyse the survival of patients in a clinical trial, the model allows isolating the effects of the treatment from the effects of other variables.

The Cox model may also be referred as to proportional hazards regression analysis. In particular, this model is a regression analysis of the survival times (or more specifically, the so-called hazard function) with respect to defined variables. The hazard function is the probability that an individual will experience an event, e.g. death, within a small time interval, given that the individual has survived up to the beginning of the interval. It can therefore be interpreted as the risk of dying at time t. The quantity hO (t) is the baseline or underlying hazard function and corresponds to the probability of dying (or reaching an event) when all the defined variables are zero. The baseline hazard function is analogous to the intercept in ordinary regression (since exp0=1). The regression coefficient β gives the proportional change that can be expected in the hazard, related to changes in the defined variables. The coefficient β is estimated by a statistical method called maximum likelihood. In survival analysis, the hazard ratio (HR) (Hazard Ratio=exp(3)) is the ratio of the hazard rates corresponding to the conditions described by two sets of defined variables. For example, in a drug study, the treated population may die at twice the rate per unit time as the control population. The hazard ratio would be 2, indicating higher hazard of death from the treatment.

Predetermined reference values, such as PREL or PRV, which are used for comparison purposes may consist of "cut-off" values.

For example, each reference ("cut-off") value PREL for each gene or protein may be determined by carrying out a method comprising the following steps:

a) providing a collection of samples from patients suffering from multiple myeloma;

b) determining the expression level of the relevant gene or protein for each sample contained in the collection provided at step a);

c) ranking the samples according to said expression level;

d) classifying said samples in pairs of subsets of increasing, respectively decreasing, number of members ranked according to their expression level;

e) providing, for each sample provided at step a), information relating to the actual clinical outcome for the corresponding cancer patient (i.e. the duration of the disease-free survival (DFS), or the event free survival (EFS) or the overall survival (OS) or both);

f) for each pair of subsets of tumour tissue samples, obtaining a Kaplan Meier percentage of survival curve;

g) for each pair of subsets of tumour tissue samples calculating the statistical significance (p value) between both subsets;

h) selecting as reference value PREL for the expression level, the value of expression level for which the p value is the smallest.

Illustratively, the expression level of a gene or a protein of interest may be assessed for 100 samples of 100 patients. The 100 samples are ranked according to the expression level of said given gene or protein. Sample 1 may have the highest expression level and sample 100 may have the lowest expression level. A first grouping provides two subsets: on one side sample Nr 1 and on the other side the 99 other samples. The next grouping provides on one side samples 1 and 2 and on the other side the 98 remaining samples etc., until the last grouping: on one side samples 1 to 99 and on the other side sample Nr 100. According to the information relating to the actual clinical outcome for the corresponding cancer patient, Kaplan Meier curves may be prepared for each of the 99 groups of two subsets. Also for each of the 99 groups, the p value between both subsets was calculated. The reference value PREL is then selected such as the discrimination based on the criterion of the minimum p value is the strongest. In other words, the expression level corresponding to the boundary between both subsets for which the p value is minimum is considered as the reference value. It should be noted that according to the experiments made by the inventors, the reference value PREL is not necessarily the median value of expression levels.

The man skilled in the art also understands that the same technique of assessment of the PRV could be used for obtaining the reference value and thereafter for assessment of the response to the combination treatment of the present invention. However in one embodiment, the reference value PRV is the median value of PRV.

In certain embodiments, the regression β coefficient reference value, the hazard ratio and the reference value PREP for each gene or protein of interest is described in Table 1 below.

TABLE 1

Relevant parameter value for each of the 15 genes of interest.

| Name | PREL | p value | Hazard Ratio | Beta Coef. |
|---|---|---|---|---|
| ARRB1 | 427 | 0.0018 | 0.22 | −2.1844246 |
| CACNA1G | 280 | 0.0074 | 0.18 | −2.4739312 |
| FBLIM1 | 75 | 0.027 | 0.46 | −1.1202942 |
| FGFR1 | 122 | 0.0031 | 0.24 | −2.0588937 |
| IRF6 | 22 | 0.016 | 0.48 | −1.0588937 |
| ITGA9 | 16 | 0.0075 | 0.45 | −1.1520031 |
| NOVA2 | 89 | 0.041 | 0.16 | −2.6438562 |
| NRP2 | 126 | 0.015 | 3.4 | 1.76553475 |
| PPP2R2C | 74 | 0.017 | 0.26 | −1.9434165 |
| REEP1 | 180 | 0.005 | 2.4 | 1.26303441 |
| SLC5A1 | 158 | 0.038 | 0.41 | −1.2863042 |
| SORL1 | 52 | 0.0093 | 0.45 | −1.1520031 |
| SV2B | 208 | 0.0021 | 2.5 | 1.32192809 |
| SYT7 | 56 | 0.01 | 0.36 | −1.4739312 |
| THY1 | 48 | 0.028 | 0.5 | −1 |

In certain embodiments, the score may be generated by a computer program.

2/Identification of Multiple Myeloma Individuals that are Likely to Respond to a Therapeutic Treatment Comprising an Inhibitor of Enhancer of Zest Homologue 2 (EZH2)

Another aspect of the invention relates to a method for in vitro predicting the likelihood of an individual having a multiple myeloma to respond to a therapeutic treatment comprising an inhibitor of enhancer of zest homologue 2 (EZH2), comprising the steps of:

a) measuring the expression level of at least 5 genes and/or proteins encoded by a gene selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from an individual having a multiple myeloma;

b) calculating a score value from said expression level obtained at step a);

c) classifying the said individual as being a responsive individual or a non-responsive individual, by comparing the score value obtained at step b) with a reference score value.

Within the scope of the invention, the expression "likelihood to respond to" is meant to intend that the MM individual may be subjected to stabilization, an alleviating, a curing or a reduction of the progression of the symptoms or the disease itself.

In some embodiments, the score value may be calculated with the following formula:

$$\text{Score} = \sum_{i=1}^{n} \beta i \times Ci$$

wherein n, βi and Ci represent the same integer as previously defined above.

In some embodiments, a responsive individual refers to an individual having a score value lower than or equal to a predetermined reference value (PRV).

In some embodiments, a non-responsive individual refers to an individual having a score value higher than a predetermined reference value (PRV).

In certain embodiments, the expression level of at least 10 genes and/or proteins encoded by a gene selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

In certain preferred embodiments, the expression level of each of the 15 genes and/or proteins consisting of NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

In certain embodiments, the responsive individual is likely to respond to the said therapeutic treatment comprising an inhibitor of EZH2.

In certain embodiments, the EZH2 inhibitor is selected in a group comprising CPI-169, El-1, EPZ-005687, EPZ-6438 (Tazemetostat), GSK-126, GSK-343, GSK-503, DZNep and UNC-1999.

In some embodiments, the responsive individual is likely to respond to a combined therapeutic treatment comprising (i) an inhibitor of enhancer of zest homologue 2 (EZH2) and (ii) a further anti-MM treatment, in particular chemotherapy, a treatment with bisphosphonates, radiation, surgery, stem cell transplant and/or plasmapheresis.

In certain embodiments, the MM individual may be chosen in a group comprising MM individual general population of MM individuals, from early stage MM individuals, from intermediary stage MM individuals, from late stage MM individuals, from MM individuals not undergoing therapeutic treatment, from MM individuals not undergoing therapeutic treatment but having experienced at least one previous therapeutic treatment, from MM individuals undergoing therapeutic treatment, from MM individuals experiencing a MM relapse, and a combination thereof.

3/Identification of Multiple Myeloma Individuals that are Likely to be Resistant to a Therapeutic Treatment Comprising an Inhibitor of Enhancer of Zest Homologue 2 (EZH2)

Another aspect of the invention relates to a method for in vitro predicting the likelihood of an individual having a multiple myeloma to be resistant to a therapeutic treatment comprising an inhibitor of enhancer of zest homologue 2 (EZH2), comprising the steps of:
a) measuring the expression level of at least 5 genes and/or proteins encoded by a gene selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from an individual having a multiple myeloma;
b) calculating a score value from said expression level obtained at step a);
c) classifying the said individual as being a responsive individual or a non-responsive individual, by comparing the score value obtained at step b) with a reference score value.

Within the scope of the invention, the expression "likelihood to be resistant to" is meant to intend that the MM individual may be insensitive to stabilization, insensitive to an alleviating to a curing or to a reduction of the progression of the symptoms or the disease itself.

In some embodiments, the score value may be calculated with the following formula:

$$\text{Score} = \sum_{i=1}^{n} \beta i \times Ci$$

wherein n, βi and Ci represent the same integer as previously defined above.

In some embodiments, a non-responsive individual refers to an individual having a score value higher than or equal to a predetermined reference value (PRV).

In some embodiments, a non-responsive individual refers to an individual having a score value higher than a predetermined reference value (PRV).

In certain embodiments, the expression level of at least 10 genes and/or proteins encoded by a gene selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

In certain preferred embodiments, the expression level of each of the 15 genes and/or proteins consisting of NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

In certain embodiments, the non-responsive individual is likely to be resistant to the said therapeutic treatment comprising an inhibitor of EZH2.

In certain embodiments, the EZH2 inhibitor is selected in a group comprising CPI-169, El-1, EPZ-005687, EPZ-6438 (Tazemetostat), GSK-126, GSK-343, GSK-503, DZNep and UNC-1999.

In some embodiments, the non-responsive individual is likely to respond to a combined therapeutic treatment comprising (i) a DNA methyltransferase inhibitor and of (ii) an inhibitor of enhancer of zest homologue 2 (EZH2).

Indeed, as it is shown in the examples herein, a DNA methyltransferase inhibitor allows sensitizing human multiple myeloma cells to the action of an EZH2 inhibitor.

In some further embodiments, the non-responsive individual is likely to respond to a combined therapeutic treatment comprising (i) a DNA methyltransferase inhibitor, (ii) an inhibitor of enhancer of zest homologue 2 (EZH2) and (iii) a further anti-MM treatment, in particular chemotherapy, a treatment with bisphosphonates, radiation, surgery, stem cell transplant and/or plasmapheresis.

In some preferred embodiments, the said further anti-MM treatment is selected from the group comprising an immunomodulatory agent.

In some preferred embodiments, the said immunomodulatory agent is selected in a group comprising thalidomide, lenalidomide, pomalidomide and a derivative thereof.

In certain embodiments, the MM individual may be chosen in a group comprising MM individual general population of MM individuals, from early stage MM individuals, from intermediary stage MM individuals, from late stage MM individuals, from MM individuals not undergoing therapeutic treatment, from MM individuals not undergoing therapeutic treatment but having experienced at least one previous therapeutic treatment, from MM individuals undergoing therapeutic treatment, from MM individuals experiencing a MM relapse, and a combination thereof.

4/Determination of the Stage of a Multiple Myeloma Disease and Monitoring of MM Individual During a Therapeutic Treatment Another aspect of the invention relates to a method for in vitro determining the stage of a multiple myeloma disease in an individual having multiple myeloma, comprising the steps of:
a) measuring the expression level of at least 5 genes and/or proteins encoded by the said at least 5 genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from said individual;

b) calculating a score value from said expression levels obtained at step a);

c) classifying the said individual as being an early stage individual, an intermediate stage individual or a late stage individual, by comparing the score value obtained at step b) with a reference score value.

In certain embodiments, the expression level of at least 10 genes and/or proteins encoded by the said at least 10 genes selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

In certain preferred embodiments, the expression level of each of the 15 genes and/or proteins encoded by the said 15 genes consisting of NRP2, REEP1, SV2B, ARRB1, CACNA1G, FBLIM1, FGFR1, IRF6, ITGA9, NOVA2, PPP2R2C, SLC5A1, SORL1, SYT7 and THY1 is measured at step a).

Within the scope of the present invention, "early stage", "intermediate stage" and "late stage" may refer to one of the stage commonly used in the art to classify the individuals having a multiple myeloma with respect of the advancement of the disease.

Illustratively, the stage of the multiple myeloma disease may refer to the stage as determined by the Durie-Salmon system.

According to this system, there are three stages, stages I (1), II (2) or III (3).

For example, stage I refers to multiple myeloma without symptoms, because there are fewer cancer cells in the body. Stage I may be characterized by (i) a number of red blood cells within or slightly below normal range; (ii) normal amount of calcium in the blood; low levels of M protein in the blood or urine; M protein below g/dL for IgG; below 3 g/dL for IgA; below 4 g/24h for urinary light chain; and no bone damage on X-rays.

Stage II of multiple myeloma is featured by more cancer cells in the body of the individual. Criteria for stage II are defined as those that fit neither stage I nor stage III.

Stage III of multiple myeloma is featured by many cancer cells in the body of the individual. Stage III may be characterized by (i) anaemia, namely a haemoglobin less than 8.5 gm/dL; (ii) hypercalcemia, (iii) advanced bone damages; (iv) high levels of M protein in the blood or urine, in particular M protein above 7 g/dL for IgG, above 5 g/dL for IgA and above 12 g/24h for urinary light chain.

In some embodiments, early stage may refer to stage I according to the Durie-Salmon system.

In some embodiments, intermediate stage may refer to stage II according to the Durie-Salmon system.

In some embodiments, late stage may refer to stage III according to the Durie-Salmon system.

In certain embodiments, "early stage", "intermediate stage" and "late stage" may refer to the International Staging System (ISS), which relies upon data collected from patients with multiple myeloma worldwide. Similarly to the Durie-Salmon system, the ISS has three stages, mainly based on the measurement of the levels of the serum albumin and the serum 32 microglobulin (32-M).

Accordingly to the ISS, stage I relates to a level of β2-M of less than 3.5 mg/L and a level of albumin greater than or equal to 3.5 gm/dL. Stage II may be defined by either a level of β2-M greater than 3.5 mg/L but not greater than 5.5 mg/dL and/or a level of albumin less than 3.5 g/dL. Stage III is characterized by a level of β2-M greater than 5.5 mg/L.

In some embodiments, early stage may refer to stage I according to the ISS.

In some embodiments, intermediate stage may refer to stage II according to the ISS.

In some embodiments, late stage may refer to stage III according to the ISS.

In some embodiments, the methods disclosed herein may be used in order to stage (re-stage) the disease in individuals having a recurrent or relapsed multiple myeloma, i.e. a multiple myeloma that returns after a period of being in control, e.g. after a therapeutic treatment.

In some embodiments, the score value may be calculated with the following formula:

$$\text{Score} = \sum_{i=1}^{n} \beta i \times Ci$$

wherein n, βi and Ci represent the same integer as previously defined above.

In some embodiments, an early stage individual refers to an individual having a score value lower than or equal to a predetermined reference value 1 (PRV1).

In some embodiments, a late stage individual refers to an individual having a score value higher than a predetermined reference value 2 (PRV2).

In some embodiments, an intermediate stage individual refers to an individual having a score value higher than the predetermined reference value 1 (PRV1) but lower than or equal to a predetermined reference value 2 (PRV2).

In another aspect, the invention relates to a method for in vitro monitoring the efficacy of a therapeutic treatment against a multiple myeloma disease in an individual in need thereof, comprising the steps of:

a) measuring the expression level of at least 5 genes and/or proteins encoded by the said at least 5 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from said individual before a therapeutic treatment;

b) calculating a score value "S1" from said expression levels obtained at step a);

c) measuring the expression level of the said 5 genes and/or proteins encoded by the said 5 genes, in a biological sample obtained from said individual after a therapeutic treatment;

d) calculating a score value "S2" from said expression levels obtained at step d);

e) comparing the score value "S1" and the score value "S2";

f) determining the efficacy of said therapeutic treatment from the said comparison at step e).

In another aspect, the invention relates to a method for in vitro monitoring the efficacy of a therapeutic treatment against a multiple myeloma disease in an individual in need thereof, comprising the steps of:

a) measuring the expression level of at least 5 genes and/or proteins encoded by the said at least 5 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from said individual;

b) calculating a score value "S1" from said expression levels obtained at step a);

c) administering to said individual a therapeutic treatment against MM disease;
d) measuring the expression level of the said 5 genes and/or proteins encoded by the said 5 genes;
e) calculating a score value "S2" from said expression levels obtained at step d);
f) comparing the score value "S1" and the score value "S2";
g) determining the efficacy of said therapeutic treatment from the said comparison at step f).

In some embodiments, a score value "S1" superior or equal to a score value "S2" is indicative of an efficient therapeutic treatment, in particular with an alleviating, a curing or a reduction of the progression of the symptoms or the MM disease itself.

In some embodiments, a score value "S1" inferior to a score value "S2" is indicative of an absence of effect of the therapeutic treatment, illustrated by a progression of the symptoms or the MM disease itself.

5/Pharmaceutical Compositions

Another aspect of the invention relates to a pharmaceutical composition comprising, in a pharmaceutical acceptable vehicle, an EZH2 inhibitor and optionally an immunomodulatory agent.

A further aspect of the invention pertains to a pharmaceutical composition comprising an EZH2 inhibitor and one or more active ingredients against multiple myeloma.

The terms "active ingredient against multiple myeloma", "active agent against multiple myeloma", "anti-MM active ingredient" and "anti-MM active agent" may be interchangeably used herein.

In certain embodiments, the pharmaceutical composition comprises, in a pharmaceutical acceptable vehicle, an EZH2 inhibitor and an immunomodulatory agent.

In some embodiments, the immunomodulatory agent is an immunomodulatory drug, also referred as "IMiD", i.e. a structural and functional analogue of thalidomide.

Illustratively, IMiD compounds encompass lenalidomide, pomalidomide, and derivative thereof, as well as compounds disclosed by Knight (Semin Oncol. 2005 August; 32(4 Suppl 5):S24-30).

In certain embodiments, the immunomodulatory agent is selected in a group comprising thalidomide, lenalidomide, pomalidomide and derivatives thereof.

Within the scope of the invention, the term "derivative of" is intended to refer to a compound having structural and functional analogy with a compound of interest.

In certain embodiments, the EZH2 inhibitor is selected in a group comprising CPI-169, El-1, EPZ-005687, EPZ-6438 (Tazemetostat), GSK-126, GSK-343, GSK-503, DZNep and UNC-1999.

In certain embodiments, the EZH2 inhibitor is EPZ-6438 (Tazemetostat) and the immunomodulatory agent is lenalidomide.

In certain embodiments, especially for treating MM in individuals that have been identified as likely to be non-responsive to a EZH2 inhibitor by a prediction method as described herein, the said pharmaceutical composition comprises a combination of an EZH2 inhibitor with a DNA methyltransferase inhibitor, since it is shown in the examples herein that a DNA methyltransferase inhibitor sensitizes EZH2 inhibitor-resistant MM cells to an EZH2 inhibitor.

In some embodiments, the said DNA methyltransferase inhibitor is selected in a group comprising 5-azacytidine, zebularine, caffeic acid, chlorogenic acid, epigallocatechin gallate, CC-486, hydralazine hydrochloride, procaine hydrochloride and RG108.

In certain embodiment, the dosage regimen of both the immunomodulatory agent and the EZH2 inhibitor or the pharmaceutical composition disclosed herein is established by a physician.

It is within the skills of a physician to determine the specific therapeutically effective dosage regimen, as this dosage regimen will be dependent upon a variety of factors including, but not limited to: the stage of the multiple myeloma and the severity of the disease; the age; the body weight; general health; the sex; the diet; the time course of administration; the route of administration; the duration of the treatment; the drugs that are concomitantly administered in combination with the pharmaceutical composition within the scope of the present invention.

In some embodiments, the dosage regimen of the immunomodulatory agent and/or the EZH2 inhibitor may range from about 0.0001 mg to about 1,000 mg per adult per day. Preferably, the individual is administered with an amount of about 0.0001, 0.0005, 0.001, 0.005, 0.01, 0.05, 0.1, 0.5, 1.0, 2.5, 5.0, 7.5, 10.0, 15.0, 20.0, 25.0, 50.0, 75.0, 100, 250, 500 and 750 mg of the immunomodulatory agent and/or the EZH2 inhibitor in order to adjust the dosage regimen that is the most suitable to a particular individual in need of the treatment.

A pharmaceutical composition within the scope of the present invention may contain from about 0.01 mg to about 500 mg of the immunomodulatory agent and/or the EZH2 inhibitor, preferably from about 1 mg to about 100 mg of the immunomodulatory agent and/or the EZH2 inhibitor.

In a preferred embodiment, an effective amount of the immunomodulatory agent and/or the EZH2 inhibitor is routinely administered to an individual in need thereof, at a dosage regimen from about 0.0002 mg/kg to about 20 mg/kg of body weight per day, in particular from about 0.001 mg/kg to 7 mg/kg of body weight per day.

The optimal amount of immunomodulatory agent and/or the EZH2 inhibitor to be comprised in a pharmaceutical dosage unit according to the invention may be easily adapted by the one skilled in the art using routine known protocols or methods.

The immunomodulatory agent and/or the EZH2 inhibitor and the pharmaceutical composition comprising thereof disclosed herein may be administered by any suitable route, i.e. including, but not limited to, an oral, sublingual, buccal, subcutaneous, transdermal, topical, intraperitoneal, intramuscular, intravenous, subdermal, intrathecal and intranasal and rectal administration.

5/Therapeutic Treatment

An aspect of the invention also relates to an EZH2 inhibitor, optionally combined with an anticancer treatment, for use in treating a multiple myeloma individual in need thereof.

In some embodiments, the EZH2 inhibitor is combined with an anticancer treatment, for its use in treating a multiple myeloma individual in need thereof.

A further aspect of the invention also relates to a pharmaceutical composition comprising, in a pharmaceutical acceptable vehicle, an EZH2 inhibitor, and optionally an immunomodulatory agent, for its use in treating a multiple myeloma individual in need thereof.

In certain embodiments, the pharmaceutical composition comprises, in a pharmaceutical acceptable vehicle, an EZH2 inhibitor and an immunomodulatory agent, for its use in treating a multiple myeloma individual in need thereof.

In some embodiments, the immunomodulatory agent is selected in a group comprising thalidomide, lenalidomide, pomalidomide and a derivative thereof.

In some embodiments, the pharmaceutical composition disclosed herein may be combined with an anticancer treatment, in particular a conventional anti-MM treatment.

In certain embodiments, an anti-MM treatment may include a treatment with anticancer compounds, a treatment with bisphosphonates, radiation, surgery, stem cell transplant and/or plasmapheresis.

In some embodiments, anticancer compounds may include a chemo drug, in particular selected in a group comprising melphalan, vincristine, cyclophosphamide, etoposide, doxorubicin, liposomal doxorubicin, bendamustine.

In some embodiments, anticancer compounds may include a corticosteroid, in particular selected in a group comprising dexamethasone and prednisone.

In some embodiments, anticancer compounds may include a proteasome inhibitor, in particular selected in a group comprising bortezomib, carfilzomib and ixazomib.

In some embodiments, anticancer compounds may include a histone deacetylase (HDAC) inhibitor, in particular panobinostat.

In some embodiments, anticancer compounds may include a monoclonal antibody, in particular selected in a group comprising daratumumab and elotuzumab.

In some embodiments, the EZH2 inhibitor may be combined with the following combinations:
melphalan and prednisone;
melphalan, prednisone and thalidomide;
melphalan, prednisone and bortezomib;
vincristine, doxorubicin, and dexamethasone;
thalidomide and dexamethasone;
lenalidomide and dexamethasone;
bortezomib, doxorubicin, and dexamethasone;
bortezomib, dexamethasone, and thalidomide;
bortezomib, dexamethasone, and lenalidomide;
liposomal doxorubicin, vincristine and dexamethasone;
carfilzomib, lenalidomide, and dexamethasone
dexamethasone, cyclophosphamide, etoposide, and cisplatin;
dexamethasone, thalidomide, cisplatin, doxorubicin, cyclophosphamide, and etoposide;
dexamethasone, thalidomide, cisplatin, doxorubicin, cyclophosphamide, and etoposide and bortezomib;
panobinostat, bortezomib, and dexamethasone;
ixazomib, lenalidomide, and dexamethasone; and
elotuzumab, lenalidomide, and dexamethasone.

It is noteworthy to mention that any other suitable treatment against MM may be further envisaged.

In certain embodiments, the therapeutic treatment comprising the EZH2 inhibitor is intended to target a multiple myeloma individual that is likely to respond to the said therapeutic treatment comprising an inhibitor of EZH2, as determined by a method known is the art.

In some embodiments, the multiple myeloma individual is likely to respond to the said therapeutic treatment comprising an inhibitor of EZH2, as determined by a method for in vitro predicting the likelihood of an individual having a multiple myeloma to respond to a therapeutic treatment comprising an inhibitor of enhancer of zest homologue 2 (EZH2), described herein.

This invention further relates to a pharmaceutical composition comprising an EZH2 inhibitor for its use for treating MM in a MM individual that has been identified as being responsive to an EZH2 inhibitor by a method comprising the steps of:
a) measuring the expression level of at least 5 genes and/or proteins encoded by the said at least 5 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from an individual having a multiple myeloma;
b) calculating a score value from said expression level obtained at step a);
c) classifying the said individual as being a responsive individual, by comparing the score value obtained at step b) with a reference score value.

In some embodiments, the said pharmaceutical composition further comprises one or more other anti-MM active ingredients.

In some embodiments, the said pharmaceutical composition further comprises one or more active ingredients selected in a group comprising immunomodulatory agents and DNA methyltransferase inhibitors. Immunomodulatory agents as well as DNA methyltransferase inhibitors are described elsewhere in the present specification.

This invention further pertains to a pharmaceutical composition comprising an EZH2 inhibitor and DNA methyltransferase inhibitor for its use for treating MM in a MM individual that has been identified as being non-responsive to an EZH2 inhibitor by a method comprising the steps of:
a) measuring the expression level of at least 5 genes and/or proteins encoded by the said at least 5 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from an individual having a multiple myeloma;
b) calculating a score value from said expression level obtained at step a);
c) classifying the said individual as being a non-responsive individual, by comparing the score value obtained at step b) with a reference score value.

In some embodiments, the said pharmaceutical composition further comprises one or more other anti-MM active ingredients.

In some embodiments, the said pharmaceutical composition further comprises one or more active ingredients selected in a group comprising immunomodulatory agents.

Immunomodulatory agents are described elsewhere in the present specification.

The invention also relates to a method for treating a multiple myeloma individual in need thereof, comprising the administration of an EZH2 inhibitor, optionally in a combination with an anticancer treatment, especially in a combination with an anti-MM treatment, which includes a treatment with one more other anti-MM active ingredients.

This invention also pertains to a method for treating multiple myeloma in an individual having multiple myeloma comprising the steps of:
A) performing a method predicting the likelihood of the said individual having multiple myeloma to respond to a therapeutic treatment comprising an inhibitor of enhancer of zest homologue 2 (EZH2), comprising the steps of:
a) measuring the expression level of at least 5 genes and/or proteins encoded by the said at least 5 genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from an individual having a multiple myeloma;

b) calculating a score value from said expression level obtained at step a); c) classifying the said individual as being a responsive individual or a non-responsive individual, by comparing the score value obtained at step b) with a reference score value.

B1) if the said individual has been classified as being a responsive individual at step A), then administering to the said individual an EZH2 inhibitor, preferably in combination with one or more other anti-MM active ingredients, such as one or more immunomodulatory agent; or B2) if the said individual has been classified as being a non-responsive individual at step A), then administering to the said individual an EZH2 inhibitor in combination with one or more DNA methyltransferase inhibitor, and optionally further in combination with one or more other anti-MMM active ingredients, such as one or more immunomodulatory agents.

It shall be understood that a combined treatment with two or more active ingredients, among those described herein, does not mean in all cases that the said two or more active ingredients are administered simultaneously to an individual in need thereof.

In some embodiments, the two or more active ingredients of the said combined treatment are combined in a single pharmaceutical composition before administering the said pharmaceutical composition to the said individual in need thereof. These embodiments include those wherein the said combined treatment involves three or more active ingredients and wherein two or more active ingredients are combined in a single pharmaceutical composition.

In some other embodiments, each of the active ingredients is comprised in a separate pharmaceutical composition and the said individual is administered with each of the said separate pharmaceutical compositions.

When two or more separate pharmaceutical compositions are to be administered to the said individual in need thereof, then the said pharmaceutical compositions may be administered successively in a short period of time, e.g. a one hour or less period of time.

In some other embodiments, the said separate pharmaceutical compositions may be administered in a longer period of time, at time intervals of more than one hour.

In some further embodiments, the time intervals at which the said separate pharmaceutical compositions are administered to the said individual in need thereof may significantly vary. Illustratively, a first pharmaceutical composition is administered twice a day, whereas a second pharmaceutical composition is administered daily. Still illustratively, a first pharmaceutical composition is administered daily and a second pharmaceutical composition is administered weekly.

In some embodiments, the anticancer treatment is a treatment comprising the administration of an immunomodulatory agent, in particular thalidomide, lenalidomide, pomalidomide and a derivative thereof.

In certain embodiments, the EZH2 inhibitor may be administered prior to the immunomodulatory agent.

In certain embodiments, the combination of (i) an EZH2 inhibitor and (ii) an immunomodulatory agent may be administered concomitantly, preferably in the form of a pharmaceutical composition further comprising a pharmaceutical acceptable vehicle.

In some embodiments, the said treatment method comprises administering to the said individual in need thereof a combination of (i) an EZH2 inhibitor and (ii) a DNA methyltransferase inhibitor.

In some embodiments, (i) the EZH2 inhibitor and (ii) the DNA methyltransferase inhibitor are administered concomitantly to the individual in need thereof.

In some other embodiments, the (i) the EZH2 inhibitor and (ii) the DNA methyltransferase inhibitor are not concomitantly administered to the individual in need thereof.

In some of these other embodiments, the EZH2 inhibitor is administered prior to the DNA methyltransferase inhibitor. In some other embodiments, the DNA methyltransferase inhibitor is administered prior to the EZH2 inhibitor.

In some other embodiments, the said treatment method comprises administering to the said individual in need thereof a combination of (i) an EZH2 inhibitor, (ii) a DNA methyltransferase inhibitor and (iii) an immunomodulatory agent.

In some embodiments, the (i) the EZH2 inhibitor, (ii) the DNA methyltransferase inhibitor and (iii) the immunomodulatory agent are administered concomitantly to the individual in need thereof.

In some other embodiments, the (i) the EZH2 inhibitor, (ii) the DNA methyltransferase inhibitor and (iii) the immunomodulatory agent are not administered concomitantly to the individual in need thereof. In some of these other embodiments, the respective active ingredients are administered in a time schedule of:

a) DNA methyl transferase inhibitor, followed by EZH2 inhibitor, followed by immunomodulatory agent; or
b) EZH2 inhibitor, followed by DNA methyltransferase inhibitor, followed by immunomodulatory agent; or
c) DNA methyltransferase inhibitor, followed by immunomodulatory agent, followed by EZH2 inhibitor; or
d) EZH2 inhibitor, followed by immunomodulatory agent, followed by DNA methyltransferase inhibitor; or
e) immunomodulatory agent, followed by EZH2 inhibitor, followed by DNA methyltransferase inhibitor; or
f) immunomodulatory agent, followed by DNA methyltransferase inhibitor, followed by EZH2 inhibitor agent.

EZH2 inhibitors, DNA methyltransferase inhibitors and immunomodulatory agents are described elsewhere in the present specification.

Another aspect of the invention also relates to a method for in vitro predicting the likelihood of an individual having a multiple myeloma to respond to a therapeutic treatment comprising an inhibitor of enhancer of zest homologue 2 (EZH2) and for treating said individual, comprising the steps of:

a) measuring the expression level of at least 5 genes and/or proteins encoded by a gene, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from an individual;

b) calculating a score value from said expression level obtained at step a);

c) classifying the said individual as being a responsive individual or a non-responsive individual, by comparing the score value obtained at step b) with a reference score value;

d) treating the responsive individual with a combination of (i) an EZH2 inhibitor and (ii) an immunomodulatory agent.

6/Kits

The invention also relates to a kit for performing the methods as above described, wherein said kit comprises means for measuring the expression level of at least 5 genes and/or proteins encoded by said genes, the said genes being selected in a group comprising NRP2, REEP1, SV2B, ARRB1, CACNA1G, FBLIM1, FGFR1, IRF6, ITGA9, NOVA2, PPP2R2C, SLC5A1, SORL1, SYT7 and THY1, comprising at least 2 primers or 2 sets of primers and/or at least 2 probes or 2 sets of probes.

In a particular embodiment, the probe or set of probes are labelled as above described. The kit may also contain other suitably packaged reagents and materials needed for the particular detection protocol, including solid-phase matrices, if applicable, and standards.

The invention also relates to a kit for treating an individual having a multiple myeloma comprising:
(i) an EZH2 inhibitor, and
(ii) an anticancer agent.

The invention also relates to a kit for treating an individual having a multiple myeloma comprising:
(i) an EZH2 inhibitor, and
(ii) an immunomodulatory agent.

The invention also relates to a kit for treating an individual having a multiple myeloma comprising:
(i) an EZH2 inhibitor, and
(ii) a DNA methyltransferase inhibitor.

The invention also relates to a kit for treating an individual having a multiple myeloma comprising:
(i) an EZH2 inhibitor,
(ii) a DNA methyltransferase inhibitor, and
(iii) an immunomodulatory agent.

EZH2 inhibitors, DNA methyltransferase inhibitors and immunomodulatory agents are described elsewhere in the present specification.

In some embodiments, the anticancer agent is selected in a group comprising an immunomodulatory agent, in particular thalidomide, lenalidomide, pomalidomide or a derivative thereof; a chemo drug, in particular melphalan, vincristine, cyclophosphamide, etoposide, doxorubicin, liposomal doxorubicin or bendamustine; a corticosteroid, in particular dexamethasone or prednisone; a proteasome inhibitor, in particular bortezomib, carfilzomib or ixazomib; a histone deacetylase (HDAC) inhibitor, in particular panobinostat; a monoclonal antibody, in particular daratumumab or elotuzumab; and a combination thereof.

The invention further relates to a kit for in vitro predicting the likelihood of an individual having a multiple myeloma to respond to a therapeutic treatment comprising an inhibitor of enhancer of zest homologue 2 (EZH2) and for treating said individual, comprising:
(i) at least 2 primers or 2 sets of primers and/or at least 2 probes or 2 sets of probes;
(ii) an immunomodulatory agent, and
(iii) an EZH2 inhibitor.

The invention further concerns to a kit for in vitro predicting the likelihood of an individual having a multiple myeloma to respond to a therapeutic treatment comprising an inhibitor of enhancer of zest homologue 2 (EZH2) and for treating said individual, comprising:
(i) at least 2 primers or 2 sets of primers and/or at least 2 probes or 2 sets of probes;
(ii) a DNA methyltransferase inhibitor, and
(iii) an EZH2 inhibitor.

The invention further concerns to a kit for in vitro predicting the likelihood of an individual having a multiple myeloma to respond to a therapeutic treatment comprising an inhibitor of enhancer of zest homologue 2 (EZH2) and for treating said individual, comprising:
(i) at least 2 primers or 2 sets of primers and/or at least 2 probes or 2 sets of probes;
(ii) a DNA methyltransferase inhibitor,
(iii) an EZH2 inhibitor, and
(iv) an immunomodulatory agent.

Examples

1/Materials and Methods 1.1/Human Myeloma Cell Lines (HMCLs)

XG1, XG2, XG3, XG4, XG5, XG6, XG7, XG10, XG11, XG12, XG13, XG14, XG16, XG19, XG20 and XG21 human myeloma cell lines were obtained as described in Moreaux et al. (Haematologica 96, 574-582 (2011); and Haematologica 92, 803-811 (2007)). JJN3 was kindly provided by Dr. Van Riet (Brussels, Belgium), JIM3 by Dr. MacLennan (Birmingham, UK) and MM1S by Dr. Rosen (Chicago, USA). AMO-1, LP1, L363, U266, OPM2, and SKMM2 were purchased from DSMZ® (Braunsweig, Germany) and RPMI8226 from ATTC (Rockville, Md., USA). All HMCLs derived in our laboratory were cultured in the presence of recombinant IL-6. HMCLs were authenticated according to their short tandem repeat profiling (Barallon et al.; Vitro Cell. Dev. Biol.—Anim. 46, 727-732 (2010)) and their gene expression profiling using Affymetrix U133 plus 2.0 microarrays deposited in the ArrayExpress public database under accession numbers E-TABM-937 and E-TABM-1088.

1.2/Primary Multiple Myeloma Cells

Bone marrow samples were collected after patients' written informed consent in accordance with the Declaration of Helsinki and institutional research board approval from Heidelberg and Montpellier University hospital. In particular, bone marrows were collected from 206 patients treated with high dose Melphalan (HDM) and autologous stem cell transplantation (ASCT) and this cohort is termed in the following Heidelberg-Montpellier (HM) cohort (Hose et al. Haematologica 96, 87-95 (2011)). Patients' MMCs were purified using anti-CD138 MACS microbeads (MILTENYI BIOTECH®, Bergisch Gladbach, Germany) and their gene expression level (GEP) obtained using Affymetrix U133 plus 2.0 microarrays as described in Hose et al. (Blood 113, 4331-4340 (2009)). The CEL files and MAS5 files are available in the ArrayExpress public database (E-MTAB-372). The structural chromosomal aberrations including t(4; 14)(p16.3; q32.3) and t(11; 14)(q13; q32.3), as well as numerical aberrations including 17p13 and 1q21 gain, were assayed by fluorescence in situ hybridization (iFISH). Publicly available Affymetrix GEP (Gene Expression Omnibus, accession number GSE2658) of a cohort of 345 purified MMC from previously untreated patients from the University of Arkansas for Medical Sciences (UAMS, Little Rock, Ark.), termed in the following UAMS-TT2 cohort, were used. These patients were treated with total therapy 2 including HDM and ASCT. As iFISH data are not available for UAMS-TT2 patients, t(4; 14) translocation was evaluated using MMSET spike expression and del17p13 surrogated by TP53 probe set signal. Affymetrix data of 152 relapsed MM patients subsequently treated with bortezomib (GSE9782) from the study by Mulligan et al. were also used (Blood 109, 3177-3188 (2007)).

1.3/Cell Growth Assay

HMCLs were cultured for 15 days in RPMI 1640 medium, 10% FCS, and 2 ng/ml IL-6 (control medium) in the presence of EPZ-6438 (SELLECKCHEM®). Cell concentration and viability were assessed using trypan blue dye exclusion test. The number of metabolic-active was also determined using intracellular ATP quantitation. HMCLs were cultured for 4 days in 96-well flat-bottom microtiter plates in RPMI 1640 medium, 10% FCS, and 2 ng/ml IL-6 (control medium) in the presence of Lenalidomide. Cell growth was evaluated by quantifying intracellular ATP amount with a Cell Titer Glo Luminescent Assay (PROMEGA®, Madison, Wis.) using a Centro LB 960 luminometer (BERTHOLD TECHNOLOGIES®, Bad Wildbad, Germany).

1.4/Gene Expression Profiling and Statistical Analyses

Gene expression data were normalized with the MAS5 algorithm and analyses processed with the R.2.10.1 and bioconductor version 2.5 programs. The SAM (Significance Analysis of Microarrays) algorithm was used to identify genes differentially expressed between populations as disclosed in Moreaux, et al. (Mol. Cancer Ther. 11, 2685-2692 (2012)). Univariate and multivariate analysis of genes prognostic for patients' survival was performed using the Cox proportional hazard model. Difference in overall survival between groups of patients was assayed with a log-rank test and survival curves plotted using the Kaplan-Meier method. Gene annotation and enrichment of networks were obtained with the Ingenuity Pathways Analysis software (INGENUITY® Systems, Redwood City, Calif.).

1.5/RNA Sequencing

HMCLs were cultured for 4 days without or with 1 µM of EPZ6438 RNA samples were collected as previously described in Moreaux, et al. (Mol. Cancer Ther. 11, 2685-2692 (2012)). The RNA sequencing (RNA-seq) library preparation was done with 150 ng of input RNA using the Illumina TruSeq Stranded mRNA Library Prep Kit. Paired-end RNA-seq were performed with illumina NextSeq sequencing instrument (HELIXIO®, Clermont-Ferrand, France). RNA-seq read pairs were mapped to the reference human GRCh37 genome using the STAR aligner (Dobin et al. Bioinformatics 29, 15-21 (2013)). All statistical analyses were performed with the statistics software R (version 3.2.3) and R packages developed by BioConductor project. The expression level of each gene was summarized and normalized using DESeq2 R/Bioconductor package (Love et al. Genome Biol. 15, (2014)). Differential expression analysis was performed using DESeq2 pipeline. P values were adjusted to control the global FDR across all comparisons with the default option of the DESeq2 package. Genes were considered differentially expressed if they had an adjusted p-value of 0.05 and a fold change of 1.5. Pathway enrichment analyses were performed using the R package ReactomePA (Yu and He Mol BioSyst 12, 477-479 (2016)).

1.6/Global H3K27Me3 and IKZF1—Immunofluorescence Microscopy

After deposition on slides using a Cytospin centrifuge, cells were fixed with 4% PFA, permeabilized with 0.5% Triton in PBS and saturated with 5% bovine milk in PBS. The rabbit anti-H3K27me3 (Active Motif, #39156) and anti-IKZF1 (Santa Cruz Biotechnology H-100 sc-3039) antibodies were diluted 1/500 and 1/250 respectively in 5% bovine milk in PBS, and deposited on cytospins for 60 minutes at room temperature. Slides were washed twice and antibodies to rabbit conjugated to alexa 555 (diluted 1/500 in 5% bovine milk in PBS) were added for 60 minutes at room temperature. Slides were washed and mounted with Vectashield and 1% DAPI. Images and fluorescence were captured with a ZEISS® Axio Imager Z2 microscope (×63 objective), analyzed with Omero (omero.mri.cnrs.fr) server and ImageJ software.

1.7/Cell Cycle Analysis

HMCLs were cultured in 24-well, flat-bottomed microtiter plates at $10^5$ cells per well in RPMI1640-10% FCS or X-VIVO 20 culture medium with or without IL-6 (3 ng/mL), and EPZ-6438 (SELLECKCHEM®). The cell cycle was assessed using DAPI staining (Sigma-Aldrich) and cells in the S phase using incubation with bromodeoxyuridine (BrdU) for 1 h and labeling with an anti-BrdU antibody (APC BrdU flow kit, BD BIOSCIENCES®, San Jose, Calif., USA) according to the manufacturer's instructions.

1.8/Flow Cytometry Analysis

Cells were fixed for 10 min with Cytofix/Cytoperm (BD BIOSCIENCES®) at 4° C. The overall expression of MYC, IKZF1, IRF4, H3K27me3 was evaluated by incubating $10^5$ cells with 5VaL of an Alexa 647-conjugated mouse anti-H3K27me3 antibody (Cell Signaling, 12158S) or PE-conjugated mouse anti-IKZF1 (BD-PHARMIGEN®, 564476), rat anti-IRF4 (BIOLEGEND®, 646403) or rabbit anti-MYC (Cell Signaling, #12189) antibodies in phosphate-buffered saline (PBS) containing 2% FBS at 4° C. for 20 minutes.

For primary samples, cells were double stained with APC or PE-conjugated anti-CD138 (BECKMAN-COULTER®). Flow cytometry analysis was done on a FACScan flow cytometer (BECTON DICKINSON®, Mountain View, Calif.).

1.9/Study of Apoptosis

HMCLs were cultured in 24-well, flat-bottomed microtiter plates at $10^5$ cells per well in RPMI1640-10% FCS or X-VIVO 20 culture medium with or without IL-6 (3 ng/mL), EPZ-6438 (SELLECKCHEM®) and QVD. After 8 days of culture, cells were washed twice in PBS and apoptosis was assayed with PE-conjugated Annexin V labeling (BD PHARMIGEN®). Fluorescence was analyzed on a FACScan flow cytometer.

2/Results

2.1/Embodiment of an Informative Set of 5 Genes

The inventors have determined that a set of 5 genes that are differentially expressed in a cohort of 14 MM individuals is associated with a prognostic value of their responsiveness to the EZH2 inhibitor EPZ-6438, as shown in Table 2 below.

TABLE 2

| EZH2 responsiveness prognostic value of a set of 5 genes | | |
|---|---|---|
| MM Patients | EZ score | Response |
| 1 | 10.68303373 | 73.09002433 |
| 2 | 10.68303373 | 66.53154585 |
| 3 | 10.68303373 | 72.01158433 |
| 4 | 5.735171357 | 64.14958199 |
| 5 | 10.68303373 | 46.38826885 |
| 6 | 10.68303373 | 53.40607906 |
| 7 | 10.68303373 | 61.32555158 |
| 8 | 5.735171357 | 72.6130237 |
| 9 | 3.091315167 | 112.5231615 |
| 10 | 8.039177543 | 84.95618189 |
| 11 | 3.091315167 | 117.9705497 |
| 12 | 6.314184591 | 79.27420051 |
| 13 | 5.735171357 | 77.76384709 |
| 14 | 8.039177543 | 101.43 |

The correlation coefficient value is of −0.73 and the p value is of 0.005, which shows the high informative value of the said set of 5 genes.

2.2/EZ-Score is Associated with a Prognostic Value in Two Independent Cohorts of MM Patients The inventors observed that a set of 15 genes are differentially expressed (RNA sequencing) when MM cells are treated by EPZ-6438, an inhibitor of EZH2 DNA methylase, belonging to the Polycomb Repressice complex 2 system (see Table 3 below).

TABLE 3

Set of 15 genes that are differentially expressed upon treatment of MM cells with EPZ-6438.

| Name | ID[1] | Maxstat Cutpoint (PREL) | p value | Hazard Ratio | Beta Coeff | Prognostic |
|---|---|---|---|---|---|---|
| ARRB1 | 43511_s_at | 427 | 0.0018 | 0.22 | −2.1844246 | Good |
| CACNA1G | 211802_x_at | 280 | 0.0074 | 0.18 | −2.4739312 | Good |
| FBLIM1 | 1555480_a_at | 75 | 0.027 | 0.46 | −1.1202942 | Good |
| FGFR1 | 207822_at | 122 | 0.0031 | 0.24 | −2.0588937 | Good |
| IRF6 | 1552477_a_at | 22 | 0.016 | 0.48 | −1.0588937 | Good |
| ITGA9 | 227297_at | 16 | 0.0075 | 0.45 | −1.1520031 | Good |
| NOVA2 | 235560_at | 89 | 0.041 | 0.16 | −2.6438562 | Good |
| NRP2 | 210841_s_at | 126 | 0.015 | 3.4 | 1.76553475 | Bad |
| PPP2R2C | 228140_s_at | 74 | 0.017 | 0.26 | −1.9434165 | Good |
| REEP1 | 204364_s_at | 180 | 0.005 | 2.4 | 1.26303441 | Bad |
| SLC5A1 | 206628_at | 158 | 0.038 | 0.41 | −1.2863042 | Good |
| SORL1 | 212560_at | 52 | 0.0093 | 0.45 | −1.1520031 | Good |
| SV2B | 205551_at | 208 | 0.0021 | 2.5 | 1.32192809 | Bad |
| SYT7 | 1559956_at | 56 | 0.01 | 0.36 | −1.4739312 | Good |
| THY1 | 213869_x_at | 48 | 0.028 | 0.5 | −1 | Good |

[1]Probeset ID number.

Taking advantage of these data, an EZH2 score (EZ-score) was calculated, and challenged to assess the feasibility to predict which patient will respond to EPZ-6438 treatment. This EZ-score, based on the prognostic information of the 15 genes from Table 3, is the sum of the beta coefficients of the Cox model for each prognostic gene, weighted by −1 according to the patient MMC signal above or below the probe set maxstat value (PREL value) as described in Hose et al. (Haematologica 96, 87-95; 2011).

The value of EZ-score in normal, premalignant, or malignant plasma cells is displayed in FIG. 1. MMCs of patients had a significantly higher EZ-score than normal BMPCs or plasma cells from patients with MGUS (P<0.01). HMCLs present an even higher EZ-score compared with primary MMCs (P<0.001; FIG. 1), stressing the relative between the EZ-score and the stage of the disease.

Figure 2A:
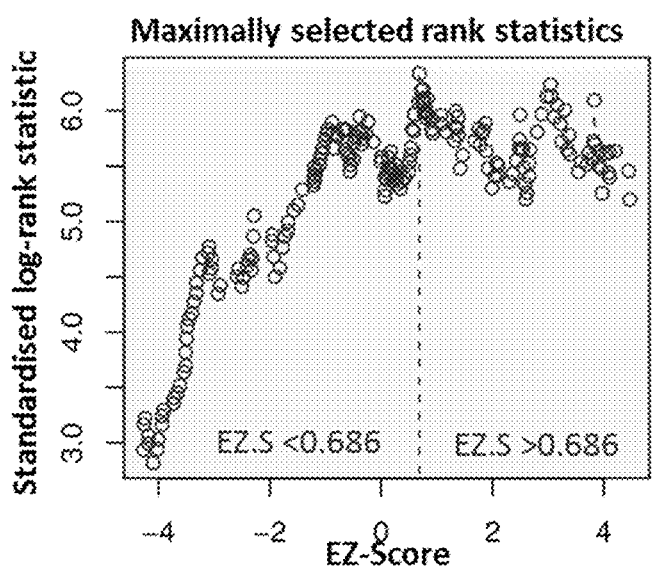
FIG. 2A: Patients of the "HM" cohort were ranked according to increased EZ score and a maximum difference in OS was obtained with EZ score of 0.686 splitting patients into high-risk (EZ score>0.686; N=153) and low-risk (EZ score<0.686; N=53) groups.
Figure 2B:
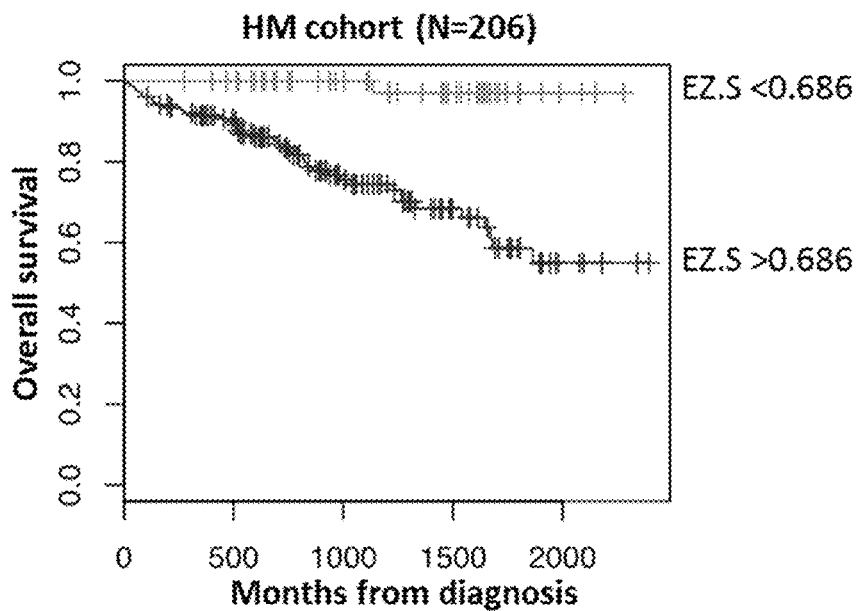
FIG. 2B: Plot illustrating the prognostic value (overall survival with respect to the months from diagnosis) of high-risk and low-risk multiple myeloma patients (HM cohort).
Figure 2C:
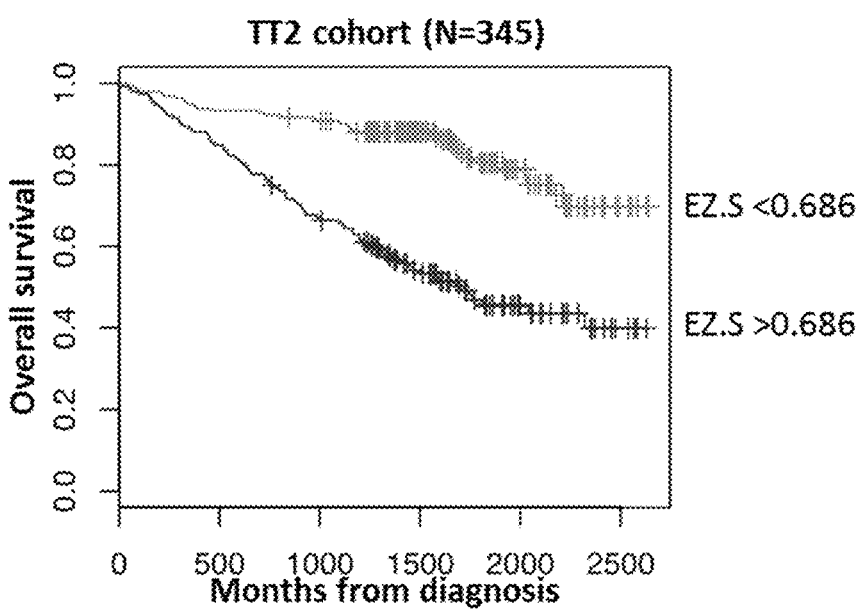
FIG. 2C: Plot illustrating the use of the EZ score also with respect to the prognostic value of an independent cohort of 345 patients from University of Arkansas for Medical Science (UAMS) treated with TT2 therapy (UAMS-TT2 cohort). The parameters to compute the EZ score of patients of UAMS-TT2 cohort and the proportions delineating the two prognostic groups were those defined with HM cohort (high-risk (EZ score>0.686; N=152) and low-risk (EZ score<0.686; N=193)).

Using patient's UAMS-TT2 cohort, EZ-score had prognostic value when used as a continuous variable or by splitting patients into 2 groups using Maxstat R function (Hose et al. Haematologica 96, 87-95; 2011). A maximum difference in OS was obtained with EZ-score splitting patients in a high-risk group of 44% of patients (EZ-score >0.686) and a low-risk group of 56% patients (EZ-score <0.686) in the TT2 cohort (P<0.0001) (FIG. 2 A). The median OS of patients within high score group (EZ-score >0.686) was 43.5 months and 50.9 for patients with low EZ-score. For each patient of HM cohort, EZ score was computed using parameters defined with patients' UAMS-TT2 cohort. Interestingly, EZ-score also has a prognostic value in the HM cohort of 206 patients (P<0.0001) (FIG. 2B).

Figure 3A:
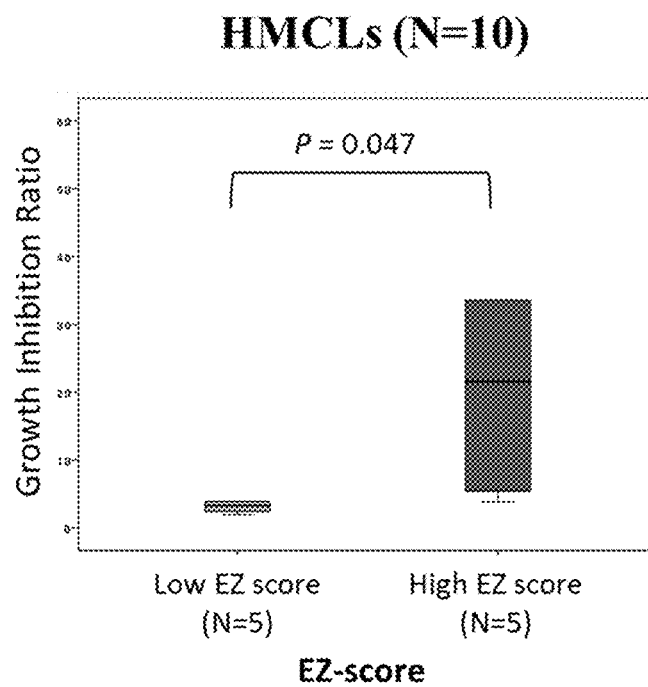
FIG. 3A: EZ score predicts for sensitivity of HMCLs and primary MMCs to EZH2 inhibitor. HMCLs with high EZ Score (N=5) exhibit significant higher EPZ-6438 sensitivity compared with HMCLs with low EZ Score (N=5). Human myeloma cell lines were cultured for 8 days in 96-well flat-bottom microtiter plates in RPMI 1640 medium, 10% fetal calf serum, 2 ng/ml IL-6 culture medium (control) and 1 µM EPZ-6438. Data are mean values±standard deviation (s.d.) of five experiments determined.

2.3/EZ Score is Predictive for Sensitivity of HMCLs or Patients' Primary MMCs to EZH2 Inhibitor In Vitro It was then sought to validate whether the EZ-score could predict for the sensitivity of 10 HMCLs to EPZ-6438. Starting from the large cohort of 40 HMCLs, the response of 5 HMCLs with a high EZ score and 5 HMCLs with a low EZ score to EPZ-6438 EZH2 inhibitor was analyzed. The 5 HMCLs with the highest EZ score exhibited a significant 20-fold median higher EPZ-6438 sensitivity compared to the 5 HMCLs with low EZ-score (P=0.04) (FIG. 3A).

Figure 3B:
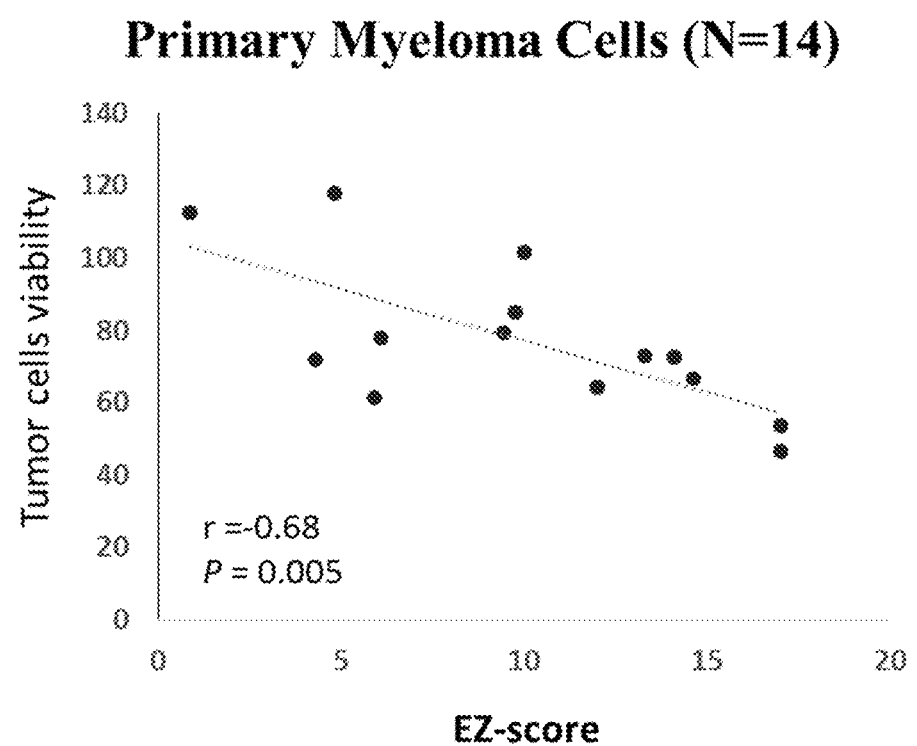
FIG. 3B: EZ score predicts for sensitivity of HMCLs and primary MMCs to EZH2 inhibitor. EZ score predicts for EPZ-6438 sensitivity of primary myeloma cells of patients. Mononuclear cells from tumor samples of 14 patients with MM were cultured for 8 days in the presence of IL-6 (2 ng/ml) with or without 1 µM EPZ-6438. At day 8 of culture, the count of viable MMCs was determined using CD138 staining by flow cytometry. A high EZ score was significantly associated with a high sensitivity of primary MM cells to EZH2 inhibitor.

To determine whether EZ score could predict the sensitivity of primary MMCs to EPZ-6438, the correlation between the toxicity of EZH2 inhibitor on MMCs and the EZ score value in a panel of 9 patients was analyzed. Primary MMCs from 14 patients were cultured together with their bone marrow environment, recombinant IL-6, and 1 μM of EPZ-6438 for 8 days. As identified with HMCLs, we identified a significant correlation between EZ score and EZH2 inhibitor activity on primary MMCs (r=−0.68; P=0.005) (FIG. 3B). Interestingly, patients exhibiting a high EZ score, associated with an adverse prognosis, are significantly more sensitive to EZH2 inhibitor treatment (FIG. 3B).

2.4/EZH2 Inhibition Sensitize Myeloma Cells to Lenalidomide

It was further investigated whether the EZH2 inhibition could enhance the anti-myeloma activity of melphalan, bortezomib and lenalidomide treatment.

Figure 4A:
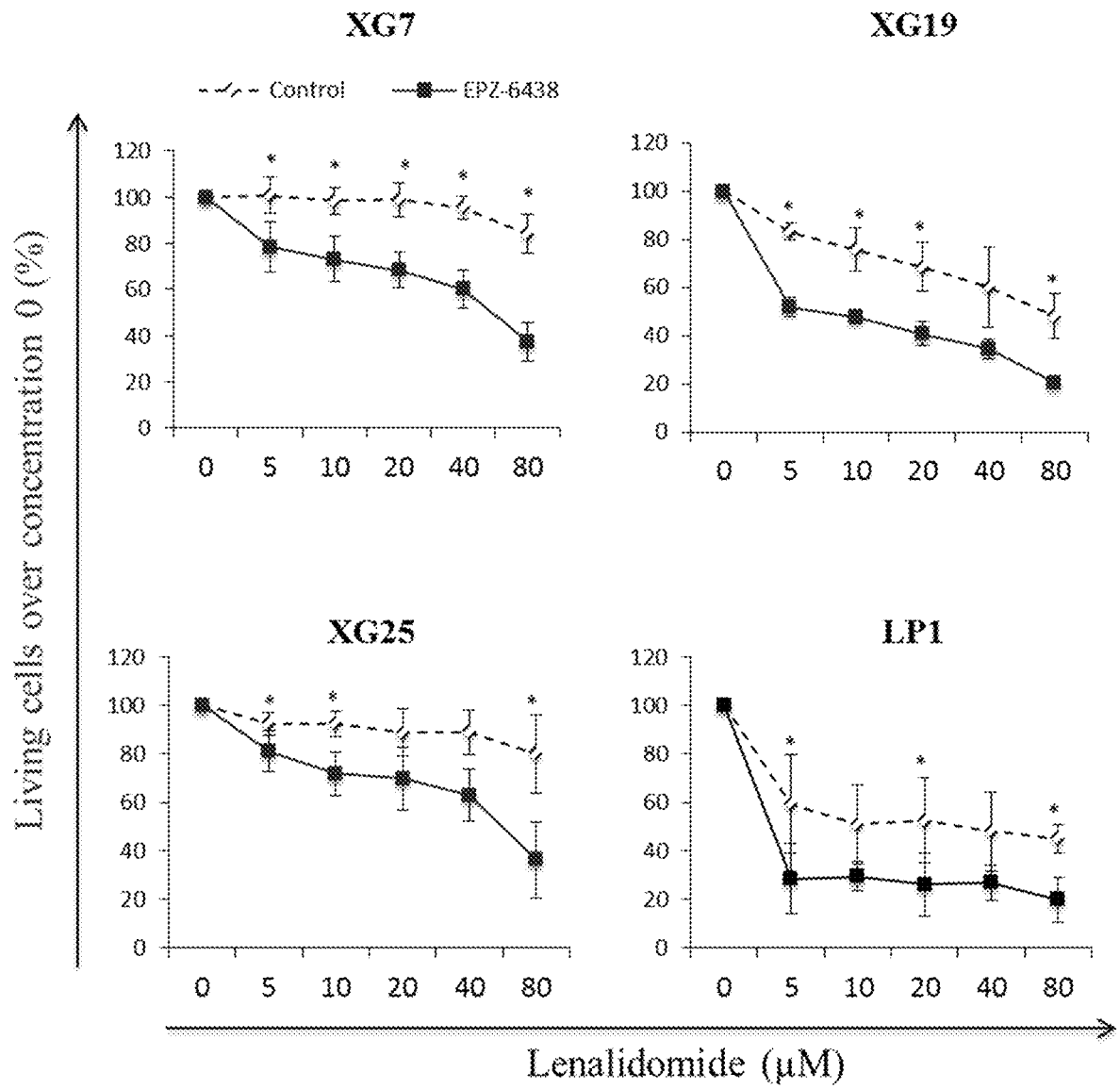
FIG. 4A: EZH2 inhibition enhances the sensibility or sensitize HMCL and primary MM cells to lenalinomide treatment. HMCLs were treated 4 days with 1 µM EPZ-6438 and then cultured 4 days in 96-well flat-bottom microtiter plates in RPMI 1640 medium, 10% fetal calf serum, 2 ng/ml IL-6 culture medium (control) and graded lenalidomide concentrations. Data are mean values±standard deviation (SD) of five experiments determined on sextuplet culture wells. * indicates a significant difference compared to control cells using a Wilcoxon test for pairs (P≤0.05).

However, EPZ-6438 pretreatment significantly sensitize myeloma cell lines to lenalidomide treatment. Myeloma cell lines were treated for 4 days with 1 uM of EPZ-6438 prior to lenalidomide treatment. EZH2 inhibitor pretreatment significantly sensitizes LP1 and XG19 lenalidomide sensitive cell lines (P<0.05) (FIG. 4A).

Furthermore, EZH2 inhibition was able to overcome IMiDs resistance in XG7 and XG25 lenalidomide resistant cell lines (FIG. 8A). Altogether, these data feature EZH2 inhibitor and IMiDs combination of clinical value in MM.

Figure 4B:
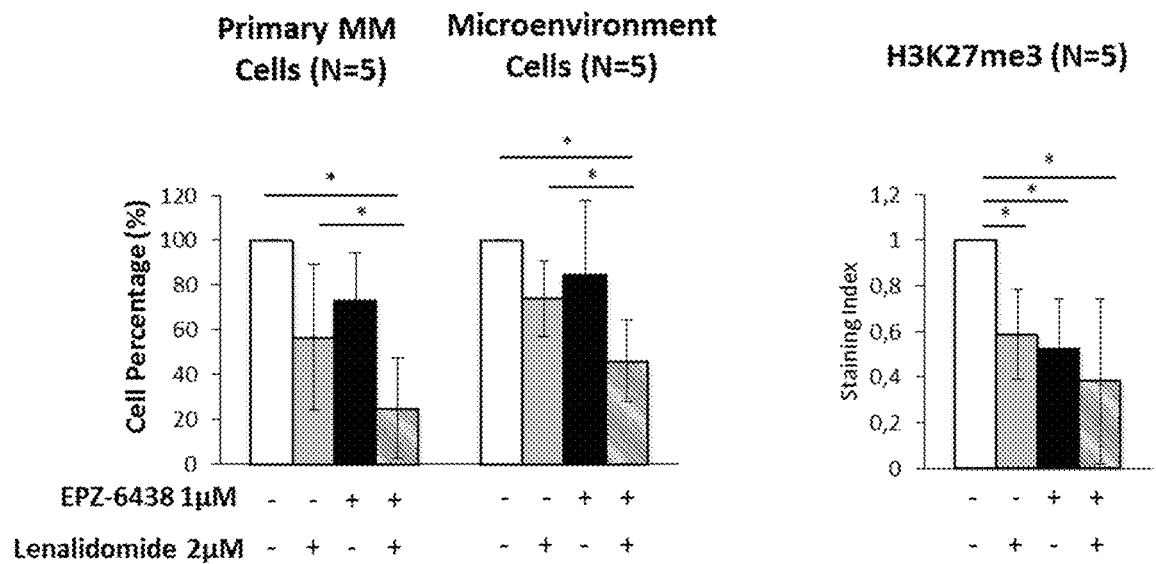
FIG. 4B: EZH2 inhibition enhances the sensibility or sensitize HMCL and primary MM cells to lenalinomide treatment. After a 4-day pre-treatment with EPZ-6438 (1 µM), mononuclear cells from 5 patients with MM were treated for four days with 2 µM lenalidomide. The viability and total cell counts were assessed and the percentage of CD138 viable plasma cells and non-malignant bone marrow cells was determined by flow cytometry. Results are median values of the numbers of myeloma cells in the culture wells. Results were compared with a Wilcoxon test for pairs.

To confirm these results on primary MMCs from patients, bone marrow samples containing malignant MMCs, co-cultured with their bone marrow environment and recombinant IL-6, were treated with EPZ-6438 and lenalidomide combination. The median percentage of viable myeloma cells was reduced of 43.4%, 26.9% and 75.1% when cells were treated with lenalidomide, EPZ-6438 or the combination EPZ-6438/lenalidomide respectively (P=0.003; n=5) (FIG. 4B). Global H3K27me3 had the tendency to decrease under combination treatment, though not significantly. Interestingly, the toxicity of EPZ-6438/lenalidomide combination was significantly higher on primary myeloma cells compared to normal bone marrow microenvironment cells.

Figure 5A:
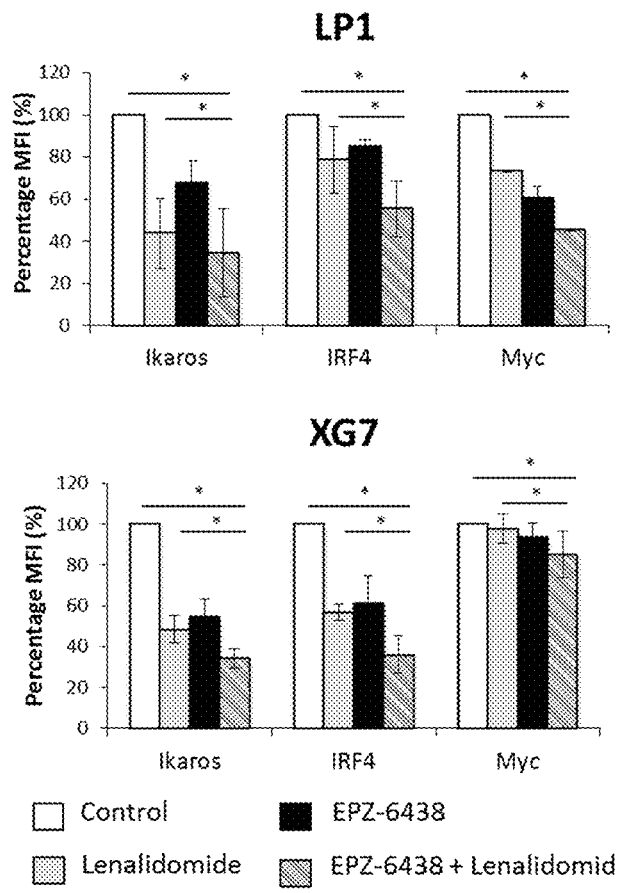
FIG. 5A: EZH2 pre-treatment enhances lenalidomide-induced IKZF1 inhibition. After 4 days of treatment with 1 µM EPZ-6438, HMCLs were cultured 2 days with or without 2 µM lenalidomide. The expression of IKZF1, c-Myc and IRF4 in HMCLs was evaluated by flow cytometry using PE-conjugated anti-IKZFL anti-MYC and anti-IRF4 mAb and isotype matched PE-conjugated mAb. Data are mean values±standard deviation (SD) of three experiments.
Figure 5B:
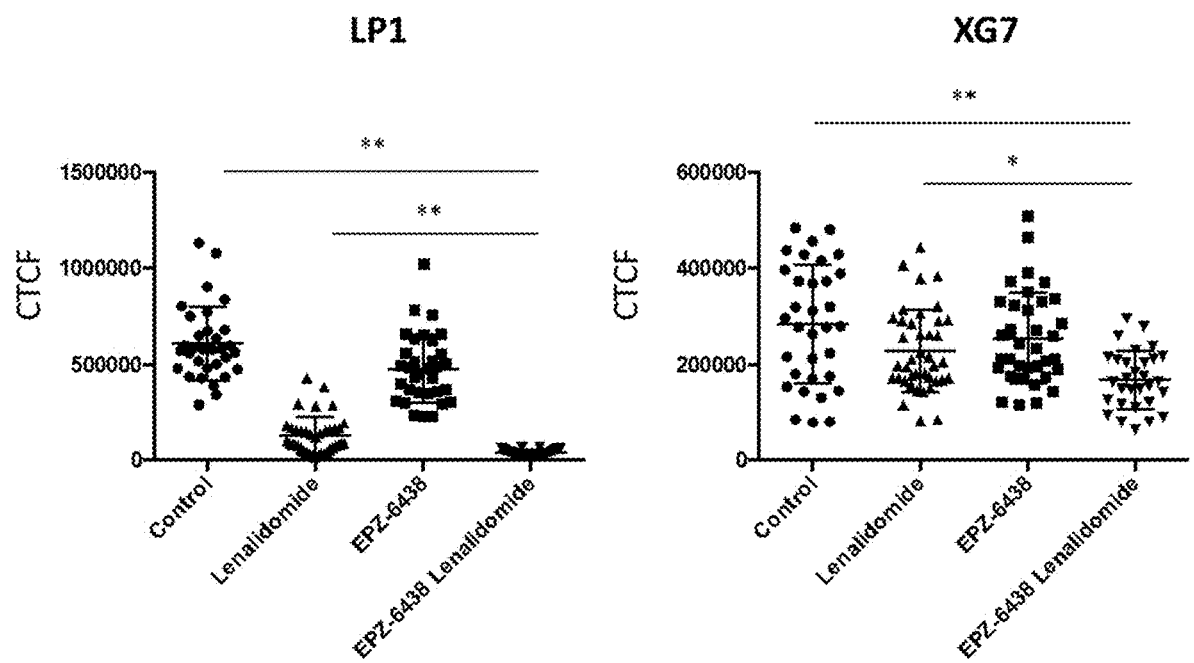
FIG. 5B: After 4 days of treatment with 1 µM EPZ-6438, HMCLs were cultured 2 days with or without 2 µM lenalidomide. The expression of IKZF1, c-Myc and IRF4 in HMCLs was evaluated by flow cytometry using PE-conjugated anti-IKZF1, anti-MYC and anti-IRF4 mAb and isotype matched PE-conjugated mAb. IKZF1 expression was assessed by immunofluorescence using an anti-IKZF1 primary antibody and an AF555-conjugated secondary antibody and further plotted onto a graph.

IMiDs promote Ikaros and Aiolos transcription factors binding to the E3 ubiquitin ligase cereblon (CRBN) leading to Ikaros and Aiolos ubiquitination and proteasomal degradation. Ikaros and Aiolos degradation are associated with a downregulation of Interferon regulatory factor 4 (IRF4) and MYC playing an essential role in MMC survival. Investigating the effect of EPZ-6438/lenalidomide combination in MMC, we identified that IKZF1, IRF4 and MYC protein levels were significantly more inhibited by the combination treatment (65.5%, 63.9% and 14.8% respectively) compared with lenalidomide (51.5%, 43% and 2.2%) or EPZ-6438 (45.2%, 38.7% and 6.2%) alone (FIGS. 5 A and B).

2.5. DNA Hypomethylating Agents Re-Sensitize EZH2 Inhibitor-Resistant Multiple Myeloma Cells fying the number assigned to each of these genes and/or proteins instead of their name.

Illustratively, each gene or protein of interest may be numbered as it follows: (1) NRP2, (2) REEP1, (3) SV2B, (4) ARRB1, (5) CACNA1G, (6) FBLIM1, (7) FGFR1, (8) IRF6, (9) ITGA9, (10) NOVA2, (11) PPP2R2C, (12) SLC5A1, (13) SORL1, (14) SYT7 and (15) THY1.

In order to further illustrate the combinations encompassed by the invention, the combinations of 2, 3, 4, 5, 6, 7, 8, 9, 10, 11, 12, 13, 14 or 15 genes and/or proteins which are explicitly considered by the invention, include any one of the 105 combinations of two selected genes and/or proteins, and which combination is represented in Table 4 here below by a "X" symbol:

| Gene and/or protein | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | | X | X | X | X | X | X | X | X | X | X | X | X | X | X |
| 2 | | | X | X | X | X | X | X | X | X | X | X | X | X | X |
| 3 | | | | X | X | X | X | X | X | X | X | X | X | X | X |
| 4 | | | | | X | X | X | X | X | X | X | X | X | X | X |
| 5 | | | | | | X | X | X | X | X | X | X | X | X | X |
| 6 | | | | | | | X | X | X | X | X | X | X | X | X |
| 7 | | | | | | | | X | X | X | X | X | X | X | X |
| 8 | | | | | | | | | X | X | X | X | X | X | X |
| 9 | | | | | | | | | | X | X | X | X | X | X |
| 10 | | | | | | | | | | | X | X | X | X | X |
| 11 | | | | | | | | | | | | X | X | X | X |
| 12 | | | | | | | | | | | | | X | X | X |
| 13 | | | | | | | | | | | | | | X | X |
| 14 | | | | | | | | | | | | | | | X |

Figure 6A:
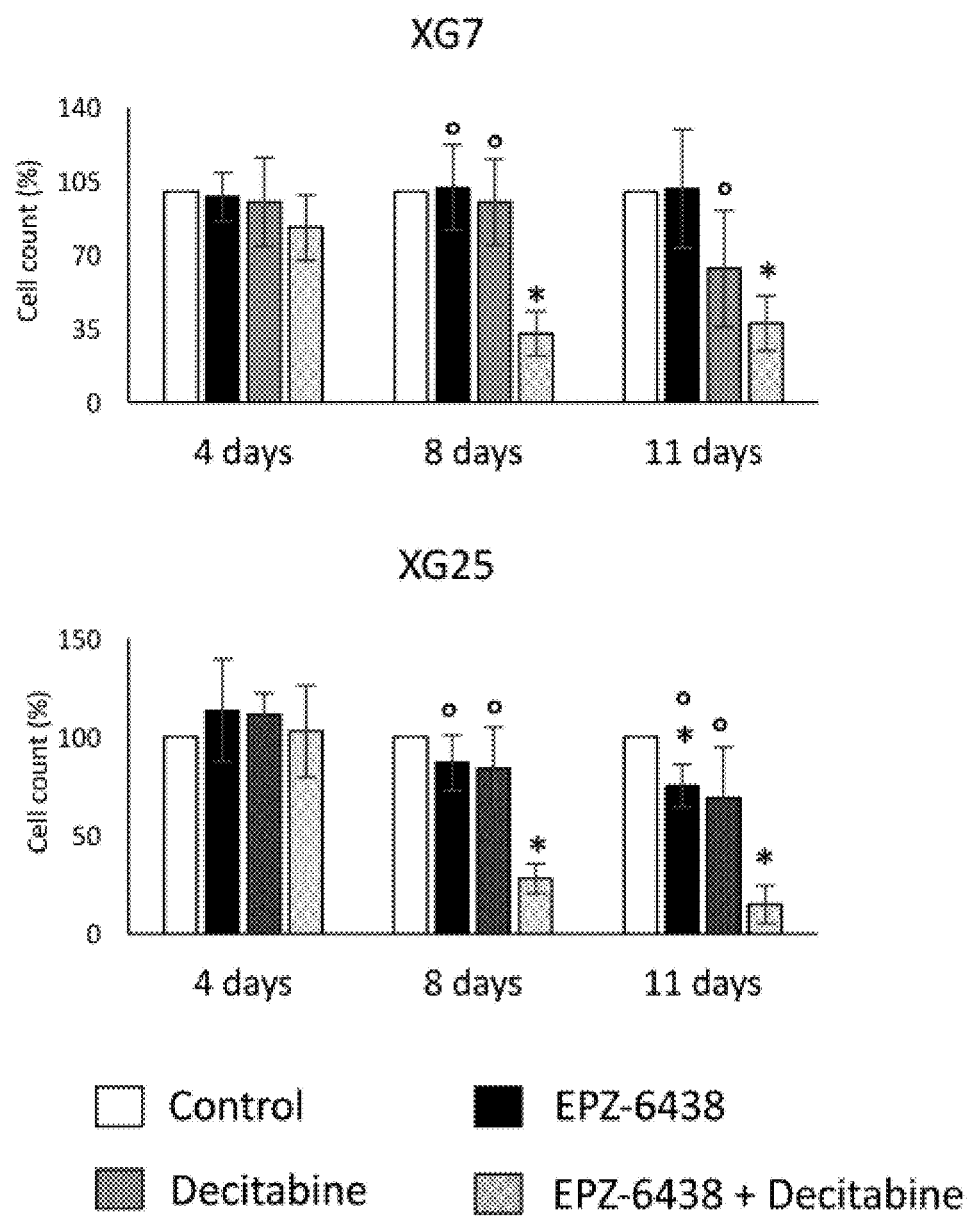
FIG. 6A: Sublethal dose of DNMTi sensitizes EPZ-6438-resistant cells to EZH2 inhibitor. Decitabine sensitize HMCLs to EPZ-6438 treatment. The HMCLs were exposed to 1 µM of EPZ-6438 and/or 100 nM of Decitabine. Cell viability was analyzed by trypan blue assay after 4, 8 and 11 days of treatment. Results are the percentage±SD of viable myeloma cells of 3 independent experiments. Statistical analysis was done with a paired t-test. * indicates a significant difference compared to control cells using a Wilcoxon test for pairs (P≤0.05). ° indicates a significant difference compared to EPZ-6438/Decitabine-treated cells using a Wilcoxon test for pairs (P≤0.05).
Figure 6B:
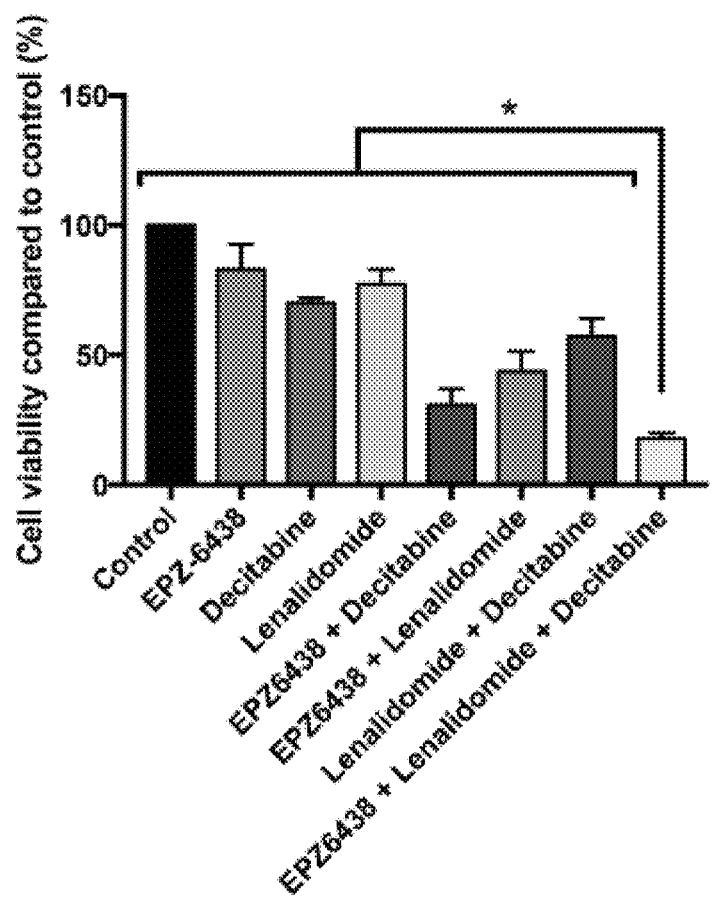
FIG. 6B Sublethal dose of DNMTi sensitizes EPZ-6438-resistant cells to EZH2 inhibitor. EPZ-6438 combined with Decitabine and Lenalidomide represents a synthetic lethality approach to target MM cells. The XG7 HMCL was exposed to 1 µM of EPZ-6438 and/or 100 nM of Decitabine and/or 5 µM of Lenalidomide. Cell viability was analyzed by trypan blue assay after 11 days of treatment. Results are the percentage±SD of viable myeloma cells of 3 independent experiments. Statistical analysis was done with a paired t-test. * indicates a significant difference compared to control cells using a Wilcoxon test for pairs (P≤0.05).

Given the fact that EZH2 target genes in MM were significantly enriched in genes upregulated by DNA hypomethylating agents (Supplementary Table S3), we compared the H3K27me3-associated genes[13] with DNA hypermethylated genes in MM patients[34]. 251 genes were found to be associated with both repressive marks (FIG. 6A and Supplementary Table S8). 68 of these genes (27%) were found to have a prognostic value in the HM cohort of previously-untreated MM patients (n=206) using the Maxstat R algorithm[30] (Supplementary Table S9). Interestingly, 89.7% of these genes were associated with a good outcome in patients (p<0.001) (Supplementary Table S9), suggesting that these repressive marks could inhibit tumor suppressor expression in MM. To assess the potential synergistic effect of the inhibition of these two repressive mechanisms, we tested the combination of a sublethal dose of Decitabine (100 nM, IC10) with EPZ-6438 (1 µM) on two EPZ-6438-resistant HMCLs. After 8 and 11 days of treatment, we observed a significant cell growth inhibition in both cell lines (67.4% and 62.4% respectively, P<0.01 in XG7, and 72.2% and 85.2% respectively in XG25), an effect stronger than when each of the drugs was added alone (P<0.05) (FIG. 6B). Therefore, DNA hypomethylation can collaborate with EZH2 inhibition to block MM cell growth.

Furthermore, the association of sublethal dose of DNMTi to EPZ-6438 and lenalidomide acts as synthetic lethality treatment in primary myeloma cells from patients (FIG. 6C).

Disclosure of the Combinations of Genes and/or Proteins

Combinations of these genes and/or proteins disclosed in the present description may be described herein by speci- When a combination of 3 genes and/or proteins are envisaged, one may start from any one of the combinations of two genes and/or proteins which are described in Table 4 above and add any one of the remaining 13 genes and/or proteins (see Table 5 below).

The first column of Table 5 indicates the combinations of two genes and/or proteins as described in Table 4; the first line of Table 5 indicates the additional gene or protein to achieve a combination of three genes and/or proteins.

| | 3 | 4 | 5 | 6 | 7 | 8 | 9 | 10 | 11 | 12 | 13 | 14 | 15 |
|---|---|---|---|---|---|---|---|---|---|---|---|---|---|
| 1 + 2 | X | X | X | X | X | X | X | X | X | X | X | X | X |
| 1 + 3 | | X | X | X | X | X | X | X | X | X | X | X | X |
| 1 + 4 | | | X | X | X | X | X | X | X | X | X | X | X |
| 1 + 5 | | | | X | X | X | X | X | X | X | X | X | X |
| 1 + 6 | | | | | X | X | X | X | X | X | X | X | X |
| 1 + 7 | | | | | | X | X | X | X | X | X | X | X |
| 1 + 8 | | | | | | | X | X | X | X | X | X | X |
| 1 + 9 | | | | | | | | X | X | X | X | X | X |
| 1 + 10 | | | | | | | | | X | X | X | X | X |
| 1 + 11 | | | | | | | | | | X | X | X | X |
| 1 + 12 | | | | | | | | | | | X | X | X |
| 1 + 13 | | | | | | | | | | | | X | X |
| 1 + 14 | | | | | | | | | | | | | X |
| 2 + 3 | | X | X | X | X | X | X | X | X | X | X | X | X |
| 2 + 4 | | | X | X | X | X | X | X | X | X | X | X | X |
| 2 + 5 | | | | X | X | X | X | X | X | X | X | X | X |
| 2 + 6 | | | | | X | X | X | X | X | X | X | X | X |
| 2 + 7 | | | | | | X | X | X | X | X | X | X | X |
| 2 + 8 | | | | | | | X | X | X | X | X | X | X |
| 2 + 9 | | | | | | | | X | X | X | X | X | X |
| 2 + 10 | | | | | | | | | X | X | X | X | X |
| 2 + 11 | | | | | | | | | | X | X | X | X |
| 2 + 12 | | | | | | | | | | | X | X | X |

-continued

| | 3 | 4 | 5 | 6 | 7 | 8 | 9 | 10 | 11 | 12 | 13 | 14 | 15 |
|---|---|---|---|---|---|---|---|---|---|---|---|---|---|
| 2 + 13 | | | | | | | | | | | | X | X |
| 2 + 14 | | | | | | | | | | | | | X |
| 3 + 4 | | | X | X | X | X | X | X | X | X | X | X | X |
| 3 + 5 | | | | X | X | X | X | X | X | X | X | X | X |
| 3 + 6 | | | | | X | X | X | X | X | X | X | X | X |
| 3 + 7 | | | | | | X | X | X | X | X | X | X | X |
| 3 + 8 | | | | | | | X | X | X | X | X | X | X |
| 3 + 9 | | | | | | | | X | X | X | X | X | X |
| 3 + 10 | | | | | | | | | X | X | X | X | X |
| 3 + 11 | | | | | | | | | | X | X | X | X |
| 3 + 12 | | | | | | | | | | | X | X | X |
| 3 + 13 | | | | | | | | | | | | X | X |
| 3 + 14 | | | | | | | | | | | | | X |
| 4 + 5 | | | | X | X | X | X | X | X | X | X | X | X |
| 4 + 6 | | | | | X | X | X | X | X | X | X | X | X |
| 4 + 7 | | | | | | X | X | X | X | X | X | X | X |
| 4 + 8 | | | | | | | X | X | X | X | X | X | X |
| 4 + 9 | | | | | | | | X | X | X | X | X | X |
| 4 + 10 | | | | | | | | | X | X | X | X | X |
| 4 + 11 | | | | | | | | | | X | X | X | X |
| 4 + 12 | | | | | | | | | | | X | X | X |
| 4 + 13 | | | | | | | | | | | | X | X |
| 4 + 14 | | | | | | | | | | | | | X |
| 5 + 6 | | | | | X | X | X | X | X | X | X | X | X |
| 5 + 7 | | | | | | X | X | X | X | X | X | X | X |
| 5 + 8 | | | | | | | X | X | X | X | X | X | X |
| 5 + 9 | | | | | | | | X | X | X | X | X | X |
| 5 + 10 | | | | | | | | | X | X | X | X | X |
| 5 + 11 | | | | | | | | | | X | X | X | X |
| 5 + 12 | | | | | | | | | | | X | X | X |
| 5 + 13 | | | | | | | | | | | | X | X |
| 5 + 14 | | | | | | | | | | | | | X |
| 6 + 7 | | | | | | X | X | X | X | X | X | X | X |
| 6 + 8 | | | | | | | X | X | X | X | X | X | X |
| 6 + 9 | | | | | | | | X | X | X | X | X | X |
| 6 + 10 | | | | | | | | | X | X | X | X | X |
| 6 + 11 | | | | | | | | | | X | X | X | X |
| 6 + 12 | | | | | | | | | | | X | X | X |
| 6 + 13 | | | | | | | | | | | | X | X |
| 6 + 14 | | | | | | | | | | | | | X |
| 7 + 8 | | | | | | | X | X | X | X | X | X | X |
| 7 + 9 | | | | | | | | X | X | X | X | X | X |
| 7 + 10 | | | | | | | | | X | X | X | X | X |
| 7 + 11 | | | | | | | | | | X | X | X | X |
| 7 + 12 | | | | | | | | | | | X | X | X |
| 7 + 13 | | | | | | | | | | | | X | X |
| 7 + 14 | | | | | | | | | | | | | X |
| 8 + 9 | | | | | | | | X | X | X | X | X | X |
| 8 + 10 | | | | | | | | | X | X | X | X | X |
| 8 + 11 | | | | | | | | | | X | X | X | X |
| 8 + 12 | | | | | | | | | | | X | X | X |
| 8 + 13 | | | | | | | | | | | | X | X |
| 8 + 14 | | | | | | | | | | | | | X |
| 9 + 10 | | | | | | | | | X | X | X | X | X |
| 9 + 11 | | | | | | | | | | X | X | X | X |
| 9 + 12 | | | | | | | | | | | X | X | X |
| 9 + 13 | | | | | | | | | | | | X | X |
| 9 + 14 | | | | | | | | | | | | | X |
| 10 + 11 | | | | | | | | | | X | X | X | X |
| 10 + 12 | | | | | | | | | | | X | X | X |
| 10 + 13 | | | | | | | | | | | | X | X |
| 10 + 14 | | | | | | | | | | | | | X |
| 11 + 12 | | | | | | | | | | | X | X | X |
| 11 + 13 | | | | | | | | | | | | X | X |
| 11 + 14 | | | | | | | | | | | | | X |
| 12 + 13 | | | | | | | | | | | | X | X |
| 12 + 14 | | | | | | | | | | | | | X |
| 13 + 14 | | | | | | | | | | | | | X |

REFERENCES

Barallon, R. et al. Recommendation of short tandem repeat profiling for authenticating human cell lines, stem cells, and tissues. *Vitro Cell. Dev. Biol. —Anim.* 46, 727-732 (2010).

Dobin, A. et al. STAR: ultrafast universal RNA-seq aligner. *Bioinformatics* 29, 15-21 (2013).

Hose, D. et al. Proliferation is a central independent prognostic factor and target for personalized and risk-adapted treatment in multiple myeloma. *Haematologica* 96, 87-95 (2011).

Hose, D. et al. Inhibition of aurora kinases for tailored risk-adapted treatment of multiple myeloma. *Blood* 113, 4331-4340 (2009).

Knight, R. IMiDs: a novel class of immunomodulators. *Semin Oncol.* 2005 August; 32(4 Suppl 5):S24-30.

Love, M. I., Huber, W. & Anders, S. Moderated estimation of fold change and dispersion for RNA-seq data with DESeq2. *Genome Biol.* 15, (2014).

Moreaux, J. et al. Development of Gene Expression-Based Score to Predict Sensitivity of Multiple Myeloma Cells to DNA Methylation Inhibitors. *Mol. Cancer Ther.* 11, 2685-2692 (2012).

Moreaux, J. et al. A high-risk signature for patients with multiple myeloma established from the molecular classification of human myeloma cell lines. *Haematologica* 96, 574-582 (2011).

Moreaux, J. et al. TACI expression is associated with a mature bone marrow plasma cell signature and C-MAF overexpression in human myeloma cell lines. *Haematologica* 92, 803-811 (2007).

Mulligan, G. et al. Gene expression profiling and correlation with outcome in clinical trials of the proteasome inhibitor bortezomib. *Blood* 109, 3177-3188 (2007).

Yu, G. & He, Q.-Y. ReactomePA: an R/Bioconductor package for reactome pathway analysis and visualization. Mol BioSyst 12, 477-479 (2016).

The invention claimed is:

1. A method for the treatment of multiple myeloma in a patient in need thereof and able to respond to an inhibitor of EZH2 comprising the steps of:
    a) identifying the patient able to respond to an inhibitor of EZH2 by
        i) determining the expression level for the genes NRP2, REEP1, SV2B, ARRB1, CACNA1G, FBLIM1, FGFR1, IRF6, ITGA9, NOVA2, PPP2R2C, SLC5A1, SORL1, SYT7 and THY1, in a biological sample obtained from the patient,
        ii) calculating a score value from said expression level obtained in step i)
        iii) comparing the said score value with a reference score value, and
        iv) confirming that the said score value calculated at step ii) is lower than or equal to the said reference score value, and concluding that the patient is able to respond to an inhibitor of EZH2; and
    b) administering the inhibitor of EZH2 to the patient, wherein the EZH2 inhibitor is selected from the group consisting of CPI-169, El-1, EPZ-005687, EPZ-6438, GSK-126, GSK-343, GSK-503, DZNep and UNC-1999.

2. The method according to claim 1, wherein step b) is administering the said inhibitor of EZH2 in combination with an immunomodulatory agent selected from the group consisting of thalidomide, lenalidomide and pomalidomide, to the patient.

3. The method according to claim 1, wherein step b) is administering the said inhibitor of EZH2 in combination with a DNA methyltransferase inhibitor selected from the group consisting of decitabine, 5-azacytidine, zebularine, caffeic acid, chlorogenic acid, epigallocatechin gallate, CC-486, hydralazine hydrochloride, procaine hydrochloride and RG108, to the patient.

4. The method according to claim 3, wherein the DNA methyltransferase inhibitor is selected from the group consisting of decitabine, 5-azacytidine, zebularine, caffeic acid and CC-486.

5. The method according to claim 1, wherein step b) is administering the said inhibitor of EZH2 in combination with a DNA methyltransferase inhibitor and an immunomodulatory agent to the patient, wherein the DNA methyltransferase is selected from the group consisting of decitabine, 5-azacytidine, zebularine, caffeic acid, chlorogenic acid, epigallocatechin gallate, CC-486, hydralazine hydrochloride, procaine hydrochloride and RG108, and wherein the immunomodulatory agent is selected from the group consisting of thalidomide, lenalidomide and pomalidomide.

6. The method according to claim 5, wherein the DNA methyltransferase inhibitor is selected from the group consisting of decitabine, 5-azacytidine, zebularine, caffeic acid and CC-486.

\* \* \* \* \*